US012559401B2

(12) United States Patent  
Rosenthal et al.

(10) Patent No.: US 12,559,401 B2  
(45) Date of Patent: Feb. 24, 2026

(54) SYSTEM AND METHOD OF GENERATING HYDROGEN GAS

(71) Applicant: Raytheon BBN Technologies, Corp., Cambridge, MA (US)

(72) Inventors: Benjamin Jacob Rosenthal, Newport, RI (US); Miles Rogers, Watertown, MA (US); Helen Scott, Watertown, MA (US)

(73) Assignee: RTX BBN TECHNOLOGIES, INC., Cambridge, MA (US)

( * ) Notice: Subject to any disclaimer, the term of this patent is extended or adjusted under 35 U.S.C. 154(b) by 1046 days.

(21) Appl. No.: 17/558,516

(22) Filed: Dec. 21, 2021

(65) Prior Publication Data

US 2022/0194786 A1     Jun. 23, 2022

Related U.S. Application Data

(60) Provisional application No. 63/128,748, filed on Dec. 21, 2020.

(51) Int. Cl.  
*C02F 3/34* (2023.01)  
*B63G 8/00* (2006.01)  
(Continued)

(52) U.S. Cl.  
CPC .............. *C02F 3/345* (2013.01); *B63G 8/001* (2013.01); *C01B 3/06* (2013.01); *C01B 17/0426* (2013.01);  
(Continued)

(58) Field of Classification Search  
CPC .. C02F 3/345; C02F 1/20; C02F 1/705; C02F 3/02; C02F 3/302; C02F 3/303;  
(Continued)

(56) References Cited

U.S. PATENT DOCUMENTS

| | | | |
|---|---|---|---|
| 5,753,110 A | 5/1998 | Matsumura et al. | |
| 6,488,998 B1 * | 12/2002 | Crook | .................... F16L 58/109 |
| | | | 138/146 |

(Continued)

FOREIGN PATENT DOCUMENTS

| | | |
|---|---|---|
| CN | 210367138 U | 4/2020 |
| CN | 112028254 A | 12/2020 |

(Continued)

OTHER PUBLICATIONS

Wang et al., Metabolic Engineering of an Aerobic Sulfate Reduction Pathway and Its Application to Precipitation of Cadmium on the Cell Surface, Applied and Environmental Microbiology, Oct. 2000, p. 4497-4502, vol. 66, No. 10, American Society for Microbiology, Washington, DC.

(Continued)

*Primary Examiner* — James A Fiorito  
(74) *Attorney, Agent, or Firm* — CANTOR COLBURN LLP

(57) ABSTRACT

A method of generating hydrogen gas includes providing a colony of sulfur-reducing bacteria and a colony of sulfur-oxidizing bacteria. The colonies can be submerged in a body of water. The colony of sulfur-reducing bacteria can be used to convert at least a portion of sulfates present in the body of water to hydrogen sulfide. The colony of sulfur-oxidizing bacteria can be used to convert the hydrogen sulfide to sulfuric acid. The sulfuric acid can react with manganese to produce hydrogen gas and manganese sulfate.

14 Claims, 9 Drawing Sheets

(51) Int. Cl.

| | |
|---|---|
| *C01B 3/06* | (2006.01) |
| *C01B 17/04* | (2006.01) |
| *C01B 17/16* | (2006.01) |
| *C01B 17/50* | (2006.01) |
| *C01B 17/74* | (2006.01) |
| *C01F 5/40* | (2006.01) |
| *C02F 1/20* | (2023.01) |
| *C02F 1/70* | (2023.01) |
| *C02F 3/02* | (2023.01) |
| *C02F 3/30* | (2023.01) |
| *C25B 1/04* | (2021.01) |
| *H01M 8/0606* | (2016.01) |
| *H01M 8/0612* | (2016.01) |
| *H01M 8/0662* | (2016.01) |
| *B63G 8/08* | (2006.01) |
| *C02F 101/10* | (2006.01) |
| *C02F 101/16* | (2006.01) |
| *C02F 101/20* | (2006.01) |
| *C02F 103/00* | (2006.01) |
| *C02F 103/08* | (2006.01) |
| *C12M 1/00* | (2006.01) |
| *C12M 1/107* | (2006.01) |
| *C12P 3/00* | (2006.01) |
| *C12R 1/01* | (2006.01) |

(52) U.S. Cl.
CPC .......... *C01B 17/164* (2013.01); *C01B 17/508* (2013.01); *C01B 17/74* (2013.01); *C01F 5/40* (2013.01); *C02F 1/20* (2013.01); *C02F 1/705* (2013.01); *C02F 3/02* (2013.01); *C02F 3/302* (2013.01); *C02F 3/303* (2013.01); *C02F 3/305* (2013.01); *C02F 3/34* (2013.01); *C02F 3/341* (2013.01); *C25B 1/04* (2013.01); *H01M 8/0606* (2013.01); *H01M 8/0631* (2013.01); *H01M 8/0662* (2013.01); *B63G 8/08* (2013.01); *C01B 2203/06* (2013.01); *C02F 2101/101* (2013.01); *C02F 2101/16* (2013.01); *C02F 2101/20* (2013.01); *C02F 2103/007* (2013.01); *C02F 2103/08* (2013.01); *C12M 21/04* (2013.01); *C12M 23/34* (2013.01); *C12P 3/00* (2013.01); *C12R 2001/01* (2021.05); *H01M 2250/20* (2013.01); *Y02E 60/50* (2013.01); *Y02T 90/40* (2013.01)

(58) Field of Classification Search
CPC .. C02F 3/305; C02F 3/34; C02F 3/341; C01B 3/06; C01B 17/164; C01B 17/74; H01M 8/0606
See application file for complete search history.

(56) References Cited

U.S. PATENT DOCUMENTS

| | | | |
|---|---|---|---|
| 2003/0113239 A1 | 6/2003 | Pahlman et al. | |
| 2005/0252214 A1 | 11/2005 | Goldmeer et al. | |
| 2005/0269263 A1 | 12/2005 | Rittmann et al. | |
| 2010/0227241 A1 | 9/2010 | Sarata et al. | |
| 2018/0170781 A1* | 6/2018 | Lupton ................... | C02F 11/02 |

FOREIGN PATENT DOCUMENTS

| | | | |
|---|---|---|---|
| EP | 0949206 A1 | 10/1999 | |
| JP | S60-148992 A | 8/1985 | |
| JP | H01-111492 A | 4/1989 | |
| JP | H05-228493 A | 9/1993 | |
| JP | 4632025 B2 | 2/2011 | |
| KR | 20040017193 A | 2/2004 | |
| KR | 101050375 B1 | 7/2011 | |
| KR | 101668549 B1 | 10/2016 | |
| KR | 102148919 B1 | 8/2020 | |
| WO | WO 2009/140428 A1 | 11/2009 | |
| WO | WO 2014/180590 A1 | 11/2014 | |
| WO | WO 2017/041028 A1 | 3/2017 | |

OTHER PUBLICATIONS

McCarty, et al. "Synthetic Biology Tools to Engineer Microbial Communities for Biotechnology", Trends in Biotechnology, Feb. 2019, vol. 37, No. 2, pp. 181-197.

Menasveta, et al., "Design and function of a closed, recirculating seawater system with denitrification for the culture of black tiger shrimp broodstock", Aquacultural Engineering vol. 25, Issue 1, pp. 35-49, 2001, 15 pages.

Peavey, "Fuel From Water Energy Dependence with Hydrogen", Merit Inc., Revised Edition, 1990, 55 pages.

Artamonova et al., Kinetics of Manganese Oxides Dissolution in Sulphuric Acid Solutions Containing Oxalic Acid, Engineering, 2013, pp. 714-719, vol. 5, Scientific Research, Atlanta, Georgia.

Bhatia et al., Biotechnological potential of microbial consortia and future perspectives, Critical Reviews in Biotechnology, May 15, 2018, 22 pages, vol. 38, No. 8, Taylor & Francis Group, Oxfordshire.

Brettin et al., RASTtk: A modular and extensible implementation of the RAST algorithm for building custom annotation pipelines and annotating batches of genomes, Scientific Reports, Feb. 10, 2015, 6 pages, vol. 5, Nature Portfolio, London.

Butler et al., Removal of Dissolved Oxygen from Water: A Comparison of Four Common Techniques, Talanta, Jan. 1, 1994, 5 pages, vol. 41, No. 2, Elsevier Science Ltd., Netherlands.

Carlson et al., Comparison of Denitrification by Pseudomonas stutzeri, Pseudomonas aeruginosa, and Paracoccus denitrificans, Applied and Environmental Microbiology, Apr. 1983, pp. 1247-1253, vol. 45, No. 4, American Society for Microbiology, Washington, DC.

Chen et al., Metabolic systems modeling for cell factories improvement, Current Opinion in Biotechnology, Aug. 1, 2017, pp. 114-119, vol. 46, Elsevier Ltd, Netherlands.

Enzelberger et al., Lipase-catalysed resolution of gamma- and delta-lactones, Journal of Biotechnology, May 28, 1997, pp. 129-133, vol. 56, No. 2, Elsevier Science B.V., Netherlands.

Haas et al., Assessment of Energy Production Potential from Ocean Currents along the United States Coastline, Georgia Tech Research Corporation Award No. DE-EE0002661, Sep. 15, 2013, 66 pages.

Huber et al., Characterization of sulfur oxidizing bacteria related to biogenic sulfuric acid corrosion in sludge digesters, BMC Microbiology, Jul. 2016, 11 pages, vol. 11, No. 1, BioMed Central, United Kingdom.

Kim et al., Recent advances in reconstruction and applications of genome-scale metabolic models, Current Opinion in Biotechnology, Aug. 2012, pp. 617-623, vol. 23, No. 4, Elsevier Ltd, Netherlands.

Konishi et al., Leaching of Marine Manganese Nodules by Acidophilic Bacteria Growing on Elemental Sulfur, Metallurgical and Materials Transactions B, Feb. 1, 1997, pp. 25-32, vol. 28, No. 1, Springer-Verlag, New York.

Li et al., Stimulating sediment bioremediation with benthic microbial fuel cells, Biotechnology Advances, Jan. 1, 2015, 12 pages, vol. 33, No. 1, Elsevier Inc., Netherlands.

Li et al., Energy-positive nitrogen removal using the integrated short-cut nitrification and autotrophic denitrification microbial fuel cells (MFCs), Applied Energy, Dec. 5, 2015, pp. 352-360, vol. 163, Elsevier Ltd, Netherlands.

Li et al., Removal of nitrogen by heterotrophic nitrification-aerobic denitrification of a phosphate accumulating bacterium *Pseudomonas stutzeri* YG-24, Bioresource Technology, 2015, pp. 18-25, vol. 182, Elsevier Ltd, Netherlands.

Liu et al., Use of genome-scale metabolic models for understanding microbial physiology, FEBS Letters, Apr. 24, 2010, pp. 2556-2564, vol. 584, No. 12, Elsevier B.V., Netherlands.

Machado et al., Fast automated reconstruction of genome-scale metabolic models for microbial species and communities, Nucleic

(56) References Cited

OTHER PUBLICATIONS

Acids Research, Jun. 21, 2018, pp. 7542-7553, vol. 46, No. 15, Oxford University Press, United Kingdom.

Mardinoglu et al., Integration of clinical data with a genome-scale metabolic model of the human adipocyte, Jan. 2013, 16 pages, vol. 9, No. 1, Molecular Systems Biology, Germany.

Mathuriya et al., Architectural adaptations of microbial fuel cells, Applied Microbiology and Biotechnology, Sep. 26, 2018, pp. 9419-9432, vol. 102, No. 22, Springer-Verlag GmbH, Germany.

Miller et al., An Overview of Seabed Mining Including the Current State of Development, Environmental Impacts, and Knowledge Gaps, Frontiers in Marine Science, Jan. 10, 2018, 24 pages, vol. 4, Frontiers Media S.A., Switzerland.

Monterey Bay Aquarium Research Institute, Sulfur, https://www3.mbari.org/chemsensor/s/sulfur.html, retrieved on Oct. 24, 2023, 1 page, retrieved from https://www3.mbari.org/chemsensor/s/sulfur.html.

Pharkya et al., OptStrain: A computational framework for redesign of microbial production systems, Genome Research, Nov. 2004, 11 pages, vol. 14, No. 11, Cold Spring Harbor Laboratory Press, Long Island, New York.

Ren et al., Population regulation in microbial consortia using dual feedback control, 2017 IEEE 56th Annual Conference on Decision and Control, 2017, 8 pages, IEEE, Piscataway, New Jersey.

Rusu et al., A review of the technologies for wave energy extraction, Clean Energy, Mar. 7, 2018, pp. 10-19, vol. 2, No. 1, Oxford University Press, United Kingdom.

Sabra et al., Biosystems analysis and engineering of microbial consortia for industrial biotechnology, Engineering in Life Sciences, Oct. 2010, pp. 407-421, vol. 10, No. 5, Wiley-VCH, Germany.

Shong et al., Towards synthetic microbial consortia for bioprocessing, Current Opinion in Biotechnology, Oct. 2012, pp. 798-802, vol. 23, No. 5, Elsevier Ltd, Netherlands.

Toro et al., Optimization of Parameters for the Dissolution of Mn from Manganese Nodules with the Use of Tailings in an Acid Medium, Jun. 26, 2019, 11 pages, MDPI, Switzerland.

Vega, Ocean Thermal Energy Conversion, Encyclopedia of Sustainability Science and Technology, Aug. 2012, pp. 7296-7328, Springer, Germany.

Vollertsen et al., Corrosion of concrete sewers—The kinetics of hydrogen sulfide oxidation, Science of the Total Environment, Feb. 20, 2008, pp. 162-170, vol. 394, No. 1, Elsevier Ltd, Netherlands.

Walker, The Whole Is More Than the Sum of the Parts: Exploiting Microbial Consortia, Industrial Biotechnology, Jun. 1, 2018, p. 107-108, vol. 14, No. 3, Mary Ann Liebert, Inc., Larchmont, New York.

Wang et al., Metabolic Engineering of an Aerobic Sulfate Reduction Pathway of Its Application to Precipitation of Cadmium on the Cell Surface, Applied and Environmental Microbiology, Oct. 2000, pp. 4497-4502, vol. 66, No. 10, American Society for Microbiology, Washington, DC.

International Search Report for International Application No. PCT/US2021/064749 dated Apr. 25, 2022, 48 pages.

Machine-generated English translation of CN 112028254, generated on Dec. 8, 2023.

Machine-generated English translation of CN 210367138, generated on Dec. 8, 2023.

Machine-generated English translation of EP 0949206, generated on Dec. 8, 2023.

Machine-generated English translation of JP 1-111492, generated on Jun. 14, 2023.

Machine-generated English translation of JP 4632025, generated on Dec. 8, 2023.

Machine-generated English translation of KR 101668549, generated on Dec. 8, 2023.

Machine-generated English translation of KR 102148919, generated on Dec. 8, 2023.

Machine-generated English translation of KR 20040017193, generated on Dec. 8, 2023.

* cited by examiner

100

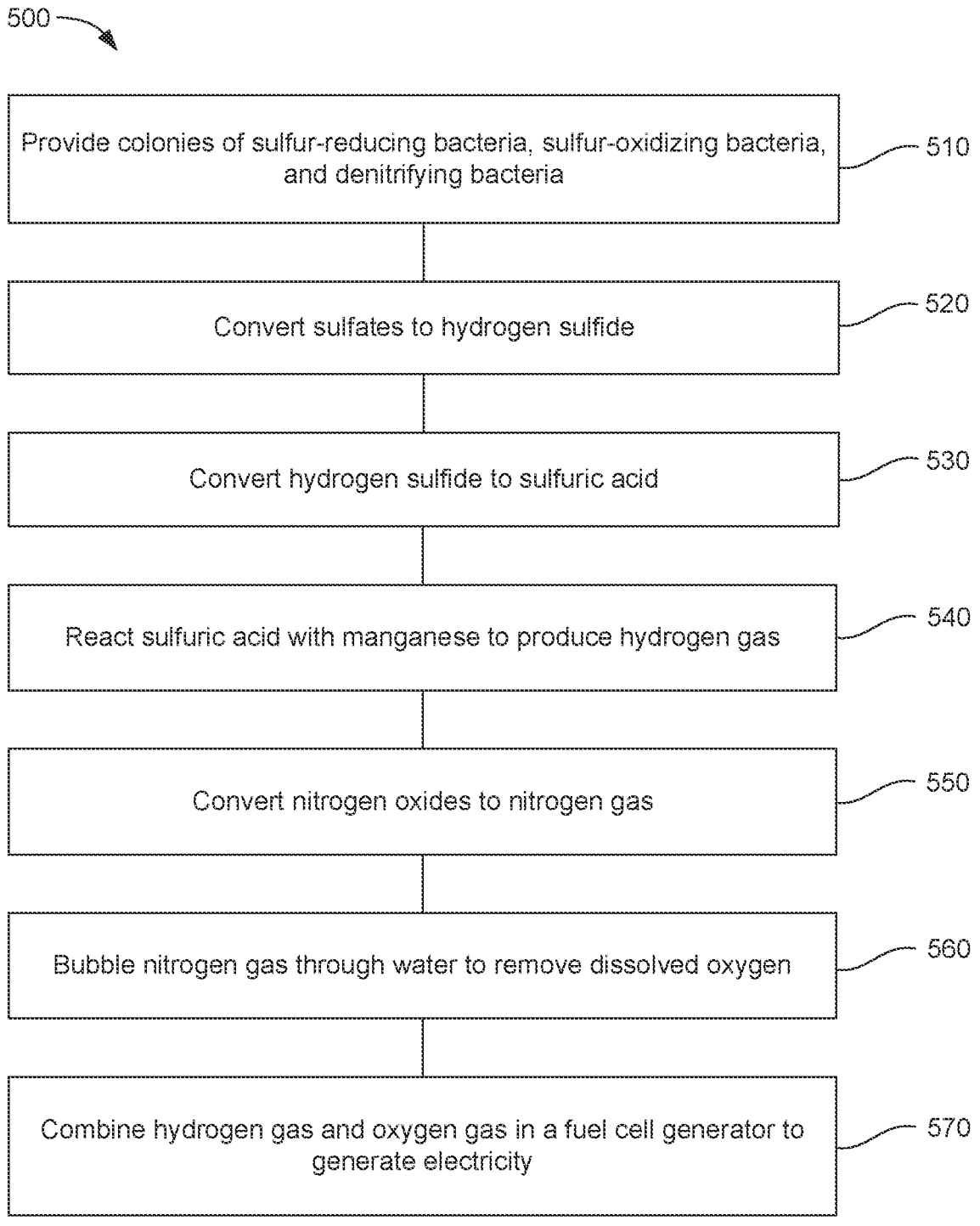

500

Provide colonies of sulfur-reducing bacteria, sulfur-oxidizing bacteria, and denitrifying bacteria — 510

Convert sulfates to hydrogen sulfide — 520

Convert hydrogen sulfide to sulfuric acid — 530

React sulfuric acid with manganese to produce hydrogen gas — 540

Convert nitrogen oxides to nitrogen gas — 550

Bubble nitrogen gas through water to remove dissolved oxygen — 560

Combine hydrogen gas and oxygen gas in a fuel cell generator to generate electricity — 570

FIG. 9

SYSTEM AND METHOD OF GENERATING HYDROGEN GAS

PRIOR APPLICATIONS

This application claims the benefit of U.S. Provisional Patent Application No. 63/128,748, filed Dec. 21, 2020, which is incorporated by reference in its entirety herein.

BACKGROUND

Unmanned, autonomous, and remote-controlled underwater vehicles are often deployed in bodies of water such as oceans. These vehicles can be used for scientific research, defense applications, and/or commercial applications such as monitoring a variety of ocean properties, marine vehicle activities, and other tasks. Many unmanned underwater vehicles propel themselves using electric motors powered by batteries. Because of the limited capacity of onboard batteries, these vehicles may have a limited range and operation time before the energy stored in the batteries is expended. In some cases, unmanned underwater vehicles can recharge batteries at a charging station on land or floating on the surface of the ocean. However, this can limit the time that the vehicles can operate at depth. Returning to the surface for recharging can be especially costly in terms of operating time for unmanned underwater vehicles that operate deep in the ocean, such as near the ocean floor.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein:

FIG. 9 is a flowchart illustrating a method of generating electricity in a body of water in accordance with an example of the present invention.

Figure 1:
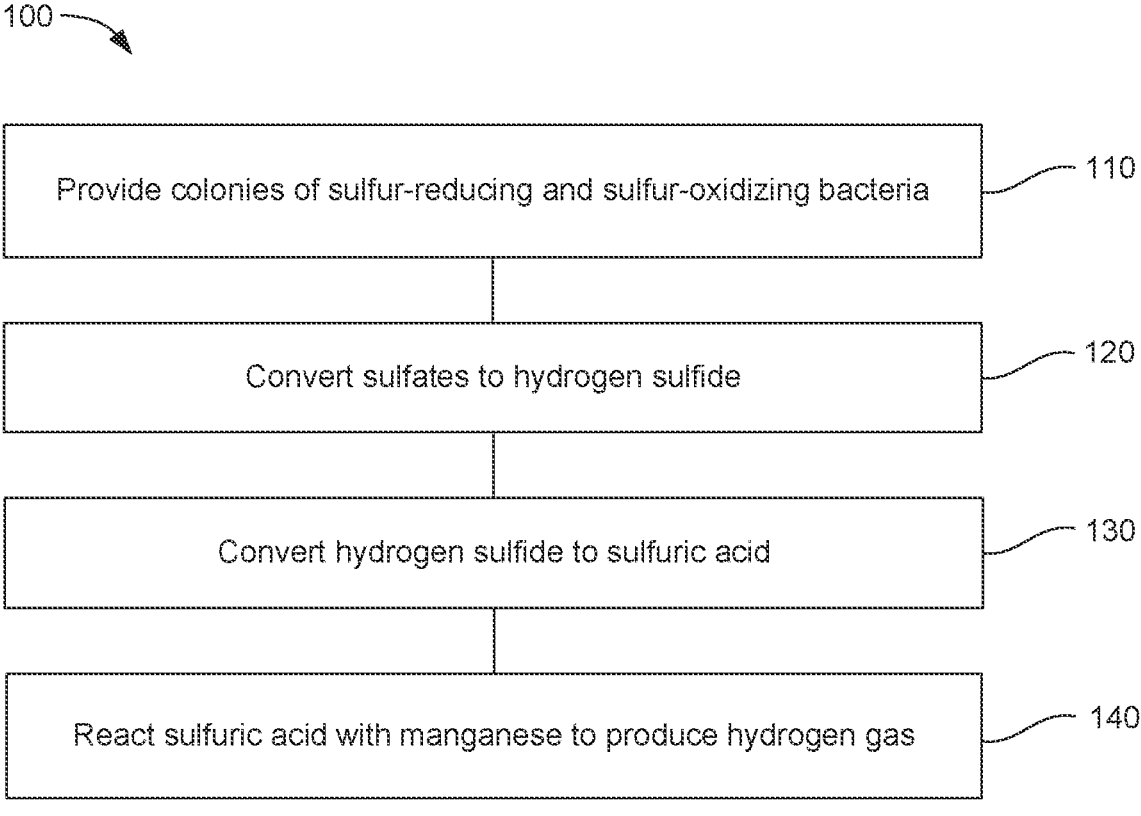
FIG. 1 is a flowchart illustrating a method of generating hydrogen gas in accordance with an example of the present invention.

Reference will now be made to the exemplary embodiments illustrated, and specific language will be used herein to describe the same. It will nevertheless be understood that no limitation of the scope of the invention is thereby intended.

DETAILED DESCRIPTION

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness can in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" can be either abutting or connected. Such elements can also be near or dose to each other without necessarily contacting each other. The exact degree of proximity can in some cases depend on the specific context.

As used herein, "colony," when referring to a colony of bacteria, means a group of bacteria. In some examples, a colony of bacteria can be a group of bacteria derived from the same mother cell. In further examples, a colony of bacteria can be grown on a solid surface and/or in the form of a biofilm, as opposed to free-floating individual bacteria. When multiple colonies of different bacteria are referred to, the colonies can be spatially separated one from another in some examples, while in other examples the colonies may occupy overlapping areas and individual bacteria from the different colonies may be intermingled.

As used herein, "body of water" refers an amount of water that is sufficiently large and deep to submerge a system as described herein. In some examples, the body of water can be a naturally-occurring body of water such as an ocean, a lake, a river, and so on. In specific examples, the body of water can be an ocean.

An initial overview of technology embodiments is provided below and then specific technology embodiments are described in further detail later. This initial summary is intended to aid readers in understanding the technology more quickly but is not intended to identify key features or essential features of the technology nor is it intended to limit the scope of the claimed subject matter.

As explained above, many electric unmanned underwater vehicles include batteries that have a limited capacity. Therefore, the batteries can be recharged periodically. The present disclosure describes methods and systems that can be useful for recharging unmanned underwater vehicles.

These systems and methods can be located at a subsurface location in a body of water, such as submerged under the surface of an ocean. The systems and methods can be used at any depth, but in certain examples it can be useful to located the systems and methods at or near the seafloor. This can be a convenient location for recharging unmanned underwater vehicles that operate near the seafloor, since the vehicles can be recharged without travelling to the ocean surface.

The systems and methods described herein can provide electrical energy by utilizing a hydrogen fuel cell generator. Hydrogen fuel cell generators produce electric current while chemically combining hydrogen and oxygen to form water. In some hydrogen fuel cells, hydrogen atoms are split into a proton and an electron using a catalyst, and the proton and electron follow different pathways to react with oxygen. The energy of the electron is harnessed as electrical energy before the electron recombines with the proton and oxygen to form a water molecule.

A hydrogen fuel cell generator can provide electrical energy as long as the hydrogen fuel is supplied with hydrogen and oxygen. Accordingly, the systems and methods described herein provide a way to obtain hydrogen gas and oxygen gas at a submerged location, such as near the seafloor. The hydrogen and oxygen can be obtained using resources that are already present in the body of water. In one example, hydrogen can be obtained by a chemical reaction of sulfuric acid with manganese. Manganese occurs naturally in the form of manganese nodules, which are mineral concretions that form naturally on the seafloor and which contain a significant amount of manganese. The systems and methods can also utilize certain bacteria to produce the sulfuric acid by converting sulfate compounds that are naturally abundant in ocean water. In another example, oxygen can be obtained by separating out naturally occurring oxygen that is dissolved in seawater. The systems and methods can separate oxygen from seawater through nitrogen purging, which is a process of flowing nitrogen gas through water to cause dissolved oxygen to migrate from the liquid water into the gas phase of the nitrogen gas. The nitrogen gas used in this process can be obtained using additional bacteria, which can convert naturally occurring nitrogen compounds in seawater into nitrogen gas. Thus, the production of hydrogen and oxygen can both be facilitated by bacteria that convert naturally occurring compounds through metabolic processes.

The bacteria utilized in the systems and methods can include any bacteria that can live in the environment where the methods are performed (i.e., seawater or water of another body of water) and which can produce the particular chemical compounds involved in the methods. As mentioned above, hydrogen gas can be produced by a chemical reaction of sulfuric acid with manganese. The sulfuric acid can be provided by at least two types of bacteria, including sulfur-reducing bacteria and sulfur-oxidizing bacteria. A variety of bacteria are capable of oxidizing sulfur compounds to form sulfuric acid. Sulfates are common in seawater, providing a limitless quantity of sulfur. However, the sulfur in sulfate is already in its highest oxidation state and therefore is unsuitable for bacterial sulfuric acid production. Therefore, sulfates can first be reduced using sulfur-reducing bacteria to form hydrogen sulfide ($H_2S$). The hydrogen sulfide can then be oxidized using sulfur-oxidizing bacteria to produce sulfuric acid. In some examples, the sulfur-reducing bacteria can produce hydrogen sulfide through an engineered aerobic sulfate reduction pathway such as pathway described in: Wang C L, Maratukulam P D, Lum A M, Clark D S, Keasling J D. Metabolic engineering of an aerobic sulfate reduction pathway and its application to precipitation of cadmium on the cell surface. *Appl Environ Microbiol.* 2000; 66(10):4497-4502. doi:10.1128/aem.66.10.4497-4502.2000. The nitrogen gas that is used to separate oxygen gas from seawater can be produce by denitrifying bacteria, which are sometimes used to remove nitrates from wastewater in wastewater purification processes. Specific types of bacteria that can be used are described in more detail below.

The hydrogen gas and oxygen gas produced by the systems and methods described herein can be used to power a hydrogen fuel cell to generate electricity. This can be done at a submerged location to provide battery charging for unmanned underwater vehicles. In certain examples, a system can produce both hydrogen gas, oxygen gas, and combine the hydrogen and oxygen in a fuel cell to generate electricity. However, in other examples, separate systems can be used to provide hydrogen gas or oxygen gas alone. Although the present disclosure focuses on the generation of hydrogen and oxygen for the purpose of powering a hydrogen fuel cell to generate electricity, there may be many other uses for hydrogen gas or oxygen gas produced at a submerged location. Therefore, in some examples, the systems and methods can provide hydrogen and/or oxygen gas as a final product for any purpose. Accordingly, the present disclosure describes multiple methods and systems that can be used separately or combined. These include: systems and methods for generating hydrogen gas; systems and methods for separating oxygen from a body of water; and systems and methods for generating electricity in a body of water.

In some examples, a method of generating hydrogen gas can include providing a colony of sulfur-reducing bacteria and a colony of sulfur-oxidizing bacteria. The colonies can be submerged in a body of water. The colony of sulfur-reducing bacteria can be used to convert at least a portion of sulfates present in the body of water to hydrogen sulfide. The colony of sulfur-oxidizing bacteria can be used to convert the hydrogen sulfide to sulfuric acid. The sulfuric acid can react with manganese to produce hydrogen gas and manganese sulfate. In some examples, the colonies can be in or on a housing submerged in the body of water. The housing can include a sulfur-reducing compartment and a sulfur-oxidizing compartment, where the colony of sulfur-reducing bacteria is in the form of a film on an interior surface of the sulfur-reducing compartment, and the colony of sulfur-oxidizing bacteria is in the form of a film on an interior surface of the sulfur-oxidizing compartment. The method can also include flowing water from the body of water into the sulfur-reducing compartment and flowing water from the sulfur-reducing compartment into the sulfur-oxidizing compartment. The housing can also include a reaction chamber, and the method can also include flowing water and the sulfuric acid from the sulfur-oxidizing compartment into the reaction chamber. The sulfuric acid can react with the manganese in the reaction chamber.

In some examples, the manganese can be in the form of a manganese nodule originating on a seafloor. The method can also include collecting the manganese nodule from the seafloor and placing the manganese nodule in the reaction chamber. The manganese nodule can be collected using a robotic collector, for example. The robotic collector can include an optical sensor to detect the manganese nodule on the seafloor based on a characteristic such as size, shape, orientation, texture, cluster density, or a combination thereof. In certain examples, the body of water can be an ocean and the colonies can be submerged at a depth within about 10 meters of a seafloor of the ocean.

In further examples, the sulfur-reducing bacteria can convert the sulfates to the hydrogen sulfide through an aerobic sulfate reduction pathway. The sulfur-reducing bacteria can include *Escherichia coli, Pseudomonas* spp., *Pseudomonas aeruginosa, Vibrio* spp., *Vibrio natriegens*, or a combination thereof. The sulfur-oxidizing bacteria can include neutrophilic sulfur-oxidizing bacteria and acidophilic sulfur-oxidizing bacteria. The neutrophilic sulfur-oxidizing bacteria can include *Thiotrix, Thiomonas, Halothiobacillus*, or a combination thereof, and wherein the acidophilic sulfur-oxidizing bacteria comprise *Acidothiobacillus thiooxidans, Acidothiobacillus ferrooxidans*, or a combination thereof.

The method of generating hydrogen gas can also include storing the hydrogen gas or using the hydrogen gas to power a hydrogen fuel cell generator to generate electricity.

In another example, a system for generating hydrogen gas can include a housing submerged or submergible in a body of water, a colony of sulfur-reducing bacteria in or on the housing to convert sulfates in the body of water to hydrogen sulfide, a colony of sulfur-oxidizing bacteria in or on the housing to convert the hydrogen sulfide to sulfuric acid, and a reaction chamber at least partially enclosed by the housing to react the sulfuric acid with manganese to produce hydrogen gas and manganese sulfate. The system can also include a robotic collector to collect a manganese nodule from a seafloor and place the manganese nodule in the reaction chamber. The robotic collector can include an optical sensor to detect the manganese nodule on the seafloor based on a characteristic such as size, shape, orientation, texture, cluster density, or a combination thereof.

The housing of the system for generating hydrogen gas can include a sulfur-reducing compartment and a sulfur-oxidizing compartment. The colony of sulfur-reducing bacteria can be in the form of a film on an interior surface of the sulfur-reducing compartment. The colony of sulfur-oxidizing bacteria can be in the form of a film on an interior surface of the sulfur-oxidizing compartment.

The sulfur-reducing bacteria can convert the sulfates to the hydrogen sulfide through an aerobic sulfate reduction pathway. The sulfur-reducing bacteria can include *Escherichia coli, Pseudomonas* spp., *Pseudomonas aeruginosa, Vibrio* spp., *Vibrio natriegens*, or a combination thereof. The sulfur-oxidizing bacteria can include neutrophilic sulfur-oxidizing bacteria and acidophilic sulfur-oxidizing bacteria. The neutrophilic sulfur-oxidizing bacteria can include *Thiotrix, Thiomonas, Halothiobacillus*, or a combination thereof, and the acidophilic sulfur-oxidizing bacteria can include *Acidothiobacillus thiooxidans, Acidothiobacillus ferrooxidans*, or a combination thereof.

As mentioned above, the present disclosure also describes methods and systems for separating oxygen from a body of water, such as seawater. In one example, a method of separating oxygen from a body of water can include providing a colony of denitrifying bacteria submerged in the body of water. The colony of denitrifying bacteria can be used to convert at least a portion of nitrogen oxides present in the body of water to nitrogen gas. The nitrogen gas can then be collected and the nitrogen gas can be bubbled through a portion of water from the body of water to remove dissolved oxygen from the portion of water, thereby forming a mixture of the nitrogen gas and oxygen gas. In some cases, the colony of denitrifying bacteria can be in or on a housing submerged in the body of water. The housing can include a denitrifying compartment and the colony of denitrifying bacteria can be in the form of a film on an interior surface of the denitrifying compartment. The housing can also include a bubbling compartment, a nitrogen collector in the denitrifying compartment to collect the nitrogen gas, and a bubble diffuser in the bubbling compartment. The bubble diffuser can be connected to the nitrogen collector to bubble the nitrogen gas through the portion of water from the body of water in the bubbling compartment. The method can also include flowing water from the body of water into the bubbling compartment to replace the volume of water in the bubbling compartment multiple times during the bubbling.

The colony of denitrifying bacteria used in the method can include *Pseudomonas, Pseudomonas* spp., *Pseudomonas stutzeri, Pseudomonas aeruginosa*, or a combination thereof. In further examples, the method can also include providing a colony of ammonia nitrifying bacteria and a colony of nitrite-oxidizing bacteria and using the colony of ammonia nitrifying bacteria and the colony of nitrite-oxidizing bacteria to convert ammonia in the body of water to nitrate. The ammonia nitrifying bacteria can include *Nitrosomonas, Nitrococcus, Nitrosospira*, or a combination thereof and the nitrite-oxidizing bacteria can include *Nitrobacter, Nitrospina, Nitrococcus, Nitrospira*, or a combination thereof.

The method of separating oxygen from a body of water can also include separating the oxygen gas from the nitrogen gas after the nitrogen gas has been used to remove the oxygen from the water. The oxygen gas can also be stored or combined with hydrogen in a hydrogen fuel cell generator to generate electricity. In some examples, the body of water can be an ocean and the colony of denitrifying bacteria can be submerged at a depth within about 10 meters of a seafloor of the ocean.

In another example, a system for separating oxygen from a body of water can include a housing submerged or submergible in the body of water, a colony of denitrifying bacteria in or on the housing to convert nitrogen oxides in the body of water to nitrogen gas, and a bubbling compartment at least partially enclosed by the housing to bubble the nitrogen gas through water from the body of water to remove dissolved oxygen from the water, thereby forming a mixture of the nitrogen gas and oxygen gas. The housing can also include a denitrifying compartment and the colony of denitrifying bacteria can be in the form of a film on an interior surface of the denitrifying compartment. Additionally, the housing can include a nitrogen collector in the denitrifying compartment to collect the nitrogen gas and a bubble diffuser in the bubbling compartment, wherein the bubble diffuser is connected to the nitrogen collector to bubble the nitrogen gas through the water from the body of water in the bubbling compartment.

In some examples, the colony of denitrifying bacteria can include *Pseudomonas, Pseudomonas* spp., *Pseudomonas stutzeri, Pseudomonas aeruginosa*, or a combination thereof. In further examples, the system can also include a colony of ammonia nitrifying bacteria in or on the housing and a colony of nitrite-oxidizing bacteria in or on the housing. The ammonia nitrifying bacteria can include *Nitrosomonas, Nitrococcus, Nitrosospira*, or a combination thereof. The nitrite-oxidizing bacteria can include *Nitrobacter, Nitrospina, Nitrococcus, Nitrospira*, or a combination thereof.

The system can also include a gas separator to separate the oxygen gas from the nitrogen gas. In some examples, the system can include an oxygen storage tank, a hydrogen fuel cell generator, or a combination thereof.

The present disclosure also describes methods and systems for generating electricity in a body of water. A method of generating electricity in a body of water can include providing a colony of sulfur-reducing bacteria, a colony of sulfur-oxidizing bacteria, and a colony of denitrifying bacteria, wherein the colonies are submerged in the body of water. The colony of sulfur-reducing bacteria can be used to convert sulfates present in the body of water to hydrogen sulfide. The colony of sulfur-oxidizing bacteria can be used to convert the hydrogen sulfide to sulfuric acid. The sulfuric acid can react with manganese to produce hydrogen gas and manganese sulfate. The colony of denitrifying bacteria can be used to convert nitrogen oxides in the body of water to nitrogen gas. The nitrogen gas can then be bubbled through a portion of water from the body of water to remove dissolved oxygen from the portion of water, thereby forming a mixture of the nitrogen gas and oxygen gas. The hydrogen gas and oxygen gas can be combined in a fuel cell generator to generate electricity.

In some examples, the colonies of bacteria can be in or on a housing submerged in the body of water. The housing can include a sulfur-reducing compartment, a sulfur-oxidizing compartment, and a denitrifying compartment. The colony of sulfur-reducing bacteria can be in the form of a film on an interior surface of the sulfur-reducing compartment. The colony of sulfur-oxidizing bacteria can be in the form of a film on an interior surface of the sulfur-oxidizing compartment. The colony of denitrifying bacteria can be in the form of a film on an interior surface of the denitrifying compartment. In some examples, the method can include flowing water from the body of water into the sulfur-reducing compartment, flowing water from the sulfur-reducing compartment into the sulfur-oxidizing compartment, and separately flowing water from the body of water into the denitrifying compartment.

In still further examples, the housing can also include a reaction chamber, and the sulfuric acid can be reacted with the manganese in the reaction chamber. The manganese can be in the form of a manganese nodule originating on a seafloor, and wherein the method can also include collecting the manganese nodule from the seafloor and placing the manganese nodule in the reaction chamber.

The method can also include storing the hydrogen gas and the oxygen gas such that the hydrogen gas and oxygen gas are combined in the hydrogen fuel cell generator to produce electricity on demand. In certain examples, the colonies and the fuel cell generator can be included in a first underwater unmanned vehicle. The method can also include docking a second underwater unmanned vehicle to the first underwater unmanned vehicle and recharging a battery of the second underwater unmanned vehicle using the electricity generated by the fuel cell generator. In other examples, the colonies can be included in a first underwater unmanned vehicle and the fuel cell generator can be included in a second underwater unmanned vehicle. In this case, the second underwater unmanned vehicle ca be dockable with the first underwater unmanned vehicle to transfer the hydrogen gas and the oxygen gas from the first underwater unmanned vehicle to the second underwater unmanned vehicle.

The sulfur-reducing bacteria can include *Escherichia coli, Pseudomonas* spp., *Pseudomonas aeruginosa, Vibrio* spp., *Vibrio natriegens*, or a combination thereof. The sulfur-oxidizing bacteria can include *Thiotrix, Thiomonas, Halothiobacillus, Acidothiobacillus thiooxidans, Acidothiobacillus ferrooxidans*, or a combination thereof. The denitrifying bacteria can include *Pseudomonas, Pseudomonas* spp., *Pseudomonas stutzeri, Pseudomonas aeruginosa*, or a combination thereof.

In some examples, the body of water can be an ocean and the colonies and the fuel cell generator can be submerged at a depth within about 10 meters of a seafloor of the ocean.

In another example, a system for generating electricity in a body of water can include a housing submerged or submergible in the body of water. A colony of sulfur-reducing bacteria can be in or on the housing to convert sulfates in the body of water to hydrogen sulfide. A colony of sulfur-oxidizing bacteria can be in or on the housing to convert the hydrogen sulfide to sulfuric acid. A reaction chamber can be at least partially enclosed by the housing to react the sulfuric acid with manganese to produce hydrogen gas and manganese sulfate. A colony of denitrifying bacteria can also be in or on the housing to convert nitrogen oxides in the body of water to nitrogen gas. A bubbling chamber can be at least partially enclosed by the housing to bubble the nitrogen gas through water from the body of water to remove dissolved oxygen from the water, thereby forming a mixture of the nitrogen gas and oxygen gas. A fuel cell generator can be connected to the reaction chamber and the bubbling chamber to combine the hydrogen gas and the oxygen gas, thereby generating electricity.

In certain examples, the housing can include a sulfur-reducing compartment, a sulfur-oxidizing compartment, and a denitrifying compartment. The colony of sulfur-reducing bacteria can be in the form of a film on an interior surface of the sulfur-reducing compartment. The colony of sulfur-oxidizing bacteria can be in the form of a film on an interior surface of the sulfur-oxidizing compartment. The colony of denitrifying bacteria can be in the form of a film on an interior surface of the denitrifying compartment.

The manganese can be in the form of a manganese nodule originating on a seafloor. The system can include a robotic collector to collect the manganese nodule from the seafloor and place the manganese nodule in the reaction chamber. In some examples, the robotic collector can include an optical sensor to detect the manganese nodule on the seafloor based on a characteristic such as size, shape, orientation, texture, cluster density, or a combination thereof.

In certain examples, the fuel cell generator and the housing can be integrated in a first underwater unmanned vehicle. In other examples, the housing can be included in a first underwater unmanned vehicle and the fuel cell generator can be included in a second underwater unmanned vehicle. The second underwater unmanned vehicle can be dockable with the first underwater unmanned vehicle to transfer the hydrogen gas and the oxygen gas from the first underwater unmanned vehicle to the second underwater unmanned vehicle.

In various examples, the sulfur-reducing bacteria can include *Escherichia coli, Pseudomonas* spp., *Pseudomonas aeruginosa, Vibrio* spp., *Vibrio natriegens*, or a combination thereof. The sulfur-oxidizing bacteria can include *Thiotix, Thiomonas, Halothiobacillus, Acidothiobacillus thiooxidans, Acidothiobacillus ferrooxidans*, or a combination thereof. The denitrifying bacteria can include *Pseudomonas, Pseudomonas* spp., *Pseudomonas stutzeri, Pseudomonas aeruginosa*, or a combination thereof.

In some examples, the system can be deployed in an ocean and submerged at a depth within about 10 meters of a seafloor of the ocean.

Systems and Methods of Generating Hydrogen Gas

An example method 100 of generating hydrogen gas is shown as a flowchart in FIG. 1. The method includes providing colonies of sulfur-reducing bacteria and sulfur-oxidizing bacteria 110; converting sulfates to hydrogen sulfide using the sulfur-reducing bacteria 120; converting hydrogen sulfide to sulfuric acid using the sulfur-oxidizing bacteria 130; and reacting the sulfuric acid with manganese to produce hydrogen gas 140. In more detail, this method can be performed at a location that is submerged in a body of water, such as an ocean. The sulfates used in the method can be naturally-occurring sulfates that are present in seawater. The manganese used in the method can be in the form of manganese nodules, which can be harvested from the seafloor. Other sources of manganese can also be used in other examples. Thus, the raw materials that are used in the method can be provided directly from the ocean environment where the method is performed.

The methods described herein can use a variety of bacteria to produce certain chemical products. As mentioned above, sulfates from the body of water can be converted to hydrogen sulfide using a colony of sulfur-reducing bacteria. The term "using" in the context of using bacteria to product a chemical product can simply mean that an appropriate starting material is provided to the bacteria, and the bacteria convert the starting material into the desired product through metabolic processes. The bacteria can perform a variety of natural or engineered metabolic processes. For example, the sulfur-reducing bacteria described herein can perform a metabolic process that converts sulfate compounds to hydrogen sulfide. When sulfates are present in the environment of the sulfur-reducing bacteria, the bacteria can take in the sulfates and metabolize the sulfates to produce hydrogen sulfide without any other stimulus or direction. Thus, the term "using" may not necessarily require any action other than providing the bacteria with an appropriate starting material to be metabolized into the desired chemical product. With this understood, it is also noted that if a starting material is converted to a product "using" bacteria, the bacteria participate in the conversion by performing a metabolic process or pathway that converts the starting material into the product. Any starting material that is converted to the desired product through some other reaction, not involving the bacteria, cannot be described as starting material that is converted to the product "using" the bacteria.

Figure 2:
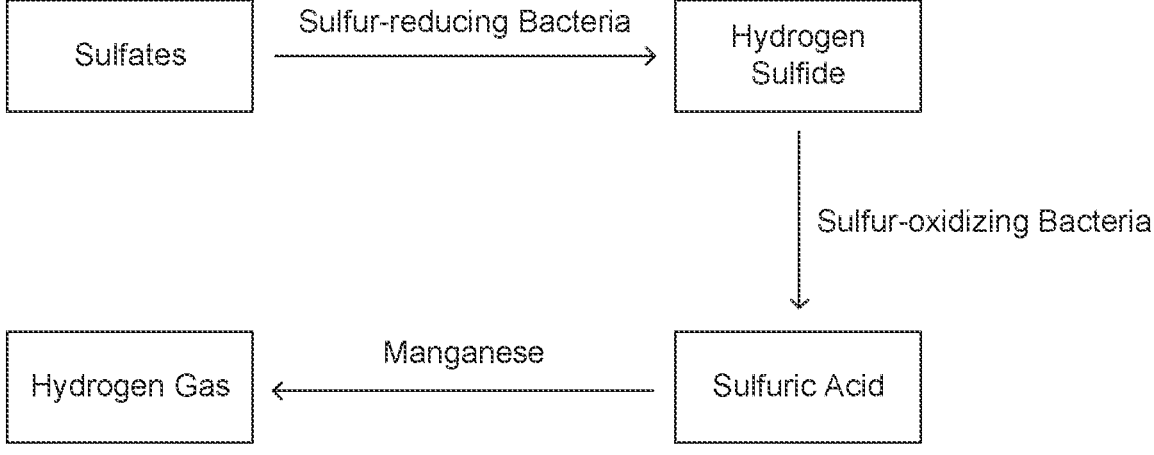
FIG. 2 is a reaction scheme showing a process of generating hydrogen gas in accordance with another example of the present invention.

FIG. 2 is a reaction scheme showing a process of generating hydrogen gas using sulfates as the starting material. The sulfates are metabolized by the sulfur-reducing bacteria to produce hydrogen sulfide. The hydrogen sulfide is then metabolized by the sulfur-oxidizing bacteria to produce sulfuric acid. The sulfuric acid chemically reacts with manganese to generate hydrogen gas. This chemical reaction also produces manganese sulfate as a byproduct.

In some examples, the chemical reactions involved in the method of generating hydrogen gas can occur in sequence, while in other examples the method can be performed in a continuous manner and the chemical reactions can occur simultaneously. In a certain example, the method can be performed as a batch process. In a batch process, a certain quantity of sulfates can be introduced to the colony of sulfur-reducing bacteria. After the sulfur-reducing bacteria have converted all the sulfates (or a desired quantity of the sulfates) to hydrogen sulfide, then the hydrogen sulfide can be introduced to the colony of sulfur-oxidizing bacteria. The sulfur-oxidizing can then be allowed to convert the hydrogen sulfide to sulfuric acid for a sufficient time to convert all or a desired quantity of the hydrogen sulfide to sulfuric acid. The sulfuric acid can then be reacted with manganese to produce hydrogen gas.

When a batch-type process is used, in some cases multiple batches can be processed simultaneously by staggering the batches with respect to the various chemical reactions that occur in the process. For example, a batch of sulfates can be converted by the colony of sulfur-reducing bacteria while a different batch of hydrogen sulfide is simultaneously converted to sulfuric acid by the colony of sulfur-oxidizing bacteria. Another batch of sulfuric acid can also be reacted with manganese as the same time. Thus, multiple batches can run in parallel in the various separate chemical reactions. In some examples, some of the chemical reactions can be performed multiple times before proceeding to the next chemical reaction in sequence. For example, multiple batches of sulfates can be converted to hydrogen sulfide and then to sulfuric acid in order to accumulate a larger quantity of sulfuric acid before the sulfuric acid is reacted with manganese. Thus, one or more parts of the methods described herein may be performed multiple times before completing the method.

The methods described herein can also operate as a continuous process. In a continuous process, the reactants and products can continuously flow from one chemical reaction to the next. For example, a stream of seawater containing sulfates can continuously flow to a colony of sulfur-reducing bacteria. The sulfur-reducing bacteria can continuously convert sulfates to hydrogen sulfide. Thus, the water surrounding the colony of sulfur-reducing bacteria can contain some amount of hydrogen sulfide. This water, with the hydrogen sulfide, can also be caused to flow to a colony of sulfur-oxidizing bacteria. The sulfur-oxidizing bacteria can convert the hydrogen sulfide to sulfuric acid. The flow of hydrogen sulfide to the colony of sulfur-oxidizing bacteria can continue while the bacteria are simultaneously metabolizing hydrogen sulfide. Water containing sulfuric acid can also be caused to flow from the colony of sulfur-oxidizing bacteria to the manganese, where the sulfuric acid can react with the manganese. This produces hydrogen gas as the final product. All of these chemical reactions can run continuously and simultaneously so that a constant stream of hydrogen gas is produced.

In still further examples, a combination or hybrid of batch and continuous-type processes can be used. For example, sulfates can be converted to hydrogen sulfide and then to sulfuric acid in a continuous manner for a period of time to accumulate a desired quantity of sulfuric acid, and then the sulfuric acid can react with a manganese nodule in a batch manner to generate hydrogen gas. In certain examples, the amount of sulfuric acid that is accumulated can be determined as the amount that will completely react with the manganese nodule. The amount of manganese can be determined by weighing the manganese nodule, for example.

The method of generating hydrogen gas can be performed at a location that is submerged in a body of water. The body of water can be a natural body of water such as an ocean, a lake, a river, and so on. In certain examples, the method can be conveniently performed in an ocean at a location where manganese nodules are available. Manganese nodules are typically found on the seafloor. Therefore, the method can be performed at or near the seafloor. More specifically, the colonies of bacteria that are used in the method can be located at or near the seafloor. The colonies of bacteria can be located at a depth within about 10 meters of the seafloor, or within about 5 meters of the seafloor, or within about 1 meter of the seafloor. In certain examples, the colonies of bacteria can be within a housing that is within 10 meters of the seafloor. The housing can be resting directly on the seafloor in some examples, or the housing can be a part of an underwater unmanned vehicle that may be resting on the seafloor, freely floating near the seafloor, or tethered to the seafloor.

In more detail regarding the bacteria used in the method of generating hydrogen gas, the method can involve a colony of sulfur-reducing bacteria and a colony of sulfur oxidizing bacteria. The colony of sulfur-reducing bacteria can include bacteria capable of converting sulfates to hydrogen sulfide. Sulfates, or more specifically the ion $SO_4^{2-}$, are naturally present in seawater and other bodies of water. The concentration of sulfate in seawater is sufficient to provide the starting material for the methods of generating hydrogen gas described herein. For example, sulfate concentration has been measured at multiple depths in the ocean and the concentration of sulfate was between about 29 and 30 millimoles of sulfate per kilogram of seawater at all depths from the ocean surface down to about 5,000 m below the surface.

In order to produce sulfuric acid to react with manganese to form hydrogen gas, the sulfates present in seawater can be converted to sulfuric acid through the colonies of bacteria described herein. A variety of sulfur-oxidizing bacteria exist that can product sulfuric acid from various sulfur compounds. However, the sulfur atom in the sulfate ion is already at is highest oxidation state and cannot be oxidized further. Therefore, the sulfate is first reduced to hydrogen sulfide, and then the hydrogen sulfide can be oxidized by sulfur-oxidizing bacteria. The reduction of sulfates has been accomplished through the use of anaerobic sulfur-reducing bacteria. These bacteria can convert sulfate to hydrogen sulfide in an anaerobic environment. However, these bacteria may not be suitable for use in an aerobic environment, such as the ocean or other natural bodies of water. Accordingly, the methods can utilize bacteria that have been engineered to reduce sulfates through an aerobic sulfate reduction pathway.

Certain bacteria have previously been engineered to use a sulfate reduction pathway can function in an aerobic environment. The engineering of bacteria to use this pathway is described in detail in the article: Wang C L, Maratukulam P D, Lum A M, Clark D S, Keasling J D. Metabolic engineering of an aerobic sulfate reduction pathway and its application to precipitation of cadmium on the cell surface. *Appl Environ Microbiol.* 2000; 66(10):4497-4502. doi:10.1128/aem.66.10.4497-4502.2000. In summary, bacteria are known to produce sulfide from sulfate during assimilatory sulfate reduction for the synthesis of cysteine and methionine. However, the assimilatory sulfate reduction is tightly regulated so that little or no excess sulfide is produced. However, bacteria were made to produce excess sulfide through two genetic changes. First, a bacterium was engineered to by changing a gene in the bacterium that caused the bacterium to overproduce cysteine. Second either the same bacterium or an additional bacterium was engineered to produce the enzyme cysteine desulfhydrase. The cysteine desulfhydrase had a high activity for converting cysteine to pyruvate, ammonia, and hydrogen sulfide. Thus, the bacteria can produce excess hydrogen sulfide through the overproduction of cysteine and the conversion of cysteine to pyruvate, ammonia, and hydrogen sulfide through the action of the cysteine desulfhydrase enzyme.

It is possible to engineer a single bacterium to perform both parts of the pathway, so that the single bacterium overproduces cysteine and also produces the cysteine desulfhydrase. However, it is also possible to use a combination of two strains of bacteria, where one strain is engineered to overproduce cysteine and the other strain is engineered to produce cysteine desulfhydrase. Furthermore, if naturally occurring bacteria can be found which naturally perform either of these parts of the pathway, then the naturally occurring bacteria can be used instead of engineered bacteria. As used herein, a "colony of sulfur-reducing bacteria" can refer to colony consisting of a single strain of bacteria that can both overproduce cysteine and produce the cysteine desulfhydrase, or to a colony comprising multiple strains of bacteria, where the strains can perform both of these functions in combination. The multiple strains of bacteria can be living in a shared area, with individual bacteria of one strain intermingled with the other strain, or the different strains can be living in separate areas that are sufficiently close together so that the cysteine and cysteine desulfhydrase can be mixed in the environment surrounding the bacteria.

In certain examples, the colony of sulfur-reducing bacteria can include bacteria of the strains described in the article by Wang et al. cited above. In other examples, different engineered bacteria strains can be made using the same aerobic sulfate reduction pathway as described in the article. In certain examples, a bacteria strain can be found that is native or well-adapted to the environment where the method of generating hydrogen gas is to be performed (such as near a seafloor in an ocean). This bacteria strain can then be used as a starting point and engineered to use the same aerobic sulfate reduction pathway described in the article.

Examples of bacteria that can be included in the colony of sulfur-reducing bacteria include: *Escherichia coli, Pseudomonas* spp., *Pseudomonas aeruginosa, Vibrio* spp., *Vibrio natriegens,* or a combination thereof. As explained above, the bacteria can be engineered to overproduce cysteine, or to produce the cysteine desulfhydrase enzyme, or both. Thus, any bacteria described herein as sulfur-reducing bacteria can be bacteria that have been engineered to use the sulfur-reducing metabolic pathway described above.

A combination of multiple different types of bacteria, used together, can be referred to a consortium. In some examples, the colony of sulfur-reducing bacteria can be a consortium including multiple different bacteria strains. Additionally, the combination of the sulfur-reducing bacteria with the sulfur-oxidizing bacteria can also be considered a consortium. In some examples, individual strains of bacteria can be selected for inclusion in a consortium based on their ability to perform a useful function in the methods of generating hydrogen gas. For example, bacteria strains that can perform a portion of the sulfate reduction pathway can be included in a consortium of bacteria that are used to reduce sulfates. To maximize the production of hydrogen gas, bacteria can be selected that are capable of performing the sulfur reduction and sulfur oxidation pathways at high rates.

In many cases, engineering bacteria to overproduce enzymes or other compounds can put a strain on the cellular metabolism of the bacteria. This can inhibit cell growth rate and overall cell health. Therefore, it can be useful to split the metabolic pathways involved in the present processes into smaller modules, such as by separating the overproduction of cysteine and the production of cysteine desulfhydrase as described above. In certain examples, the metabolic pathway can be split into these two specific modules, namely, the overproduction of cysteine and the production of cysteine desulfhydrase. The smaller modules can be expressed by different strains of bacteria in a consortium to reduce the energy burden on the individual cells. This can also allow fine-tuning of the metabolic rate of the consortium by grouping enzymes with similar turnover rates into modules. This approach can also allow bottlenecks in metabolic pathways to be reduced or eliminated. Thus, cell fitness and product yield can be increased. Consortia can also be more resilient to environmental and evolutionary perturbation compared to a single engineered strain.

As mentioned above, after sulfates have been converted to hydrogen sulfide by the colony of sulfur-reducing bacteria, a colony of sulfur-oxidizing bacteria can be used to oxidize the hydrogen sulfide to produce sulfuric acid. Similar to the colony of sulfur-reducing bacteria, the colony of sulfur-oxidizing bacteria can also consist of a single bacterial strain or can include a consortium of multiple different bacterial strains. In certain examples, the colony of sulfur-oxidizing bacteria can include neutrophilic sulfur-oxidizing bacteria and acidophilic sulfur-oxidizing bacteria. A variety of bacteria having metabolic pathways for converting hydrogen sulfide to sulfuric acid have been well-characterized. However, different bacterial strains can also be engineered to use these metabolic pathways and/or the metabolic pathways can be split up over a consortium of different bacteria as explained above. In the case of a consortium including neutrophilic sulfur-oxidizing bacteria and acidophilic sulfur-oxidizing bacteria, the neutrophilic bacteria can produce a small amount of sulfuric acid that can reduce the pH of the environment around the bacteria. For example, the sulfuric acid produced by the neutrophilic bacteria can be sufficient to reduce the pH from about 8 to between 3 and 4. This can make the environment suitable for acidophilic sulfur-oxidizing bacteria that can produce sulfuric acid in greater amounts. Acidophilic sulfur-oxidizing bacteria are often used in the mining industry to remove sulfur from waste.

In certain examples, the colony of sulfur-oxidizing bacteria can include neutrophilic bacteria such as *Thiotrix, Thiomonas, Halothiobacillus*, or a combination thereof. In further examples, the colony of sulfur-oxidizing bacteria can include acidiphilic bacteria such as *Acidothiobacillus thiooxidans, Acidothiobacillus ferrooxidans*, or a combination thereof. The colony of sulfur-oxidizing bacteria can also include a combination of any of the above neutrophilic bacteria with any of the above acidophilic bacteria. Some combinations of these bacteria have been shown to produce 24 grams of sulfuric acid in one liter of water in 12 hours. If more efficient consortia are designed, then the sulfur-oxidizing bacteria can potentially produce sulfuric acid at an even higher rate.

In some examples, the colony of sulfur-oxidizing bacteria can produce sulfuric acid in an amount of about 5 grams per liter of water to about 50 grams per liter of water, where the water is a portion of the body of water in which the method of generating hydrogen gas is performed. The water can also include hydrogen sulfide produced by the colony of sulfur-reducing bacteria.

In any of the bacterial consortia used in the methods described herein, the consortia can include natural bacteria, engineered bacteria, or a combination of both. In some cases, consortia can be designed having multiple bacterial strains that naturally occur in communities in a natural microbiome. Using combinations of bacteria that naturally live in communities can be useful in some examples since these bacterial strains are known to be compatible together. In certain examples, multiple bacterial strains from a natural community can be combined with one or more other bacterial strains that do not occur naturally in the same community. In further examples, any of the bacteria from the natural community or from outside the natural community may be engineered to alter their metabolism in order to change compounds produced by the bacteria or the rate at which certain compounds are produced by the bacteria.

When bacterial consortia are used in the methods described herein, it can be useful to maintain the ratios of the populations of different types of bacteria in certain ranges. The populations of the various bacterial strains in the consortia can be designed to produce a product compound, such as hydrogen sulfide or sulfuric acid, at a desired rate. In some examples, the consortia can have a population ratio that is maintained using orthogonal quorum sensing molecules and/or toxin/antitoxin systems. For example, each member of the consortium can produce a unique quorum sensing molecule and a unique diffusible toxin that will kill that particular bacteria in the absence of a corresponding antitoxin. The quorum sensing molecule can activate the production of the antitoxin in other members of the consortium. If an insufficient ratio exists, then too much of the toxin will be present and the overrepresented bacteria will begin to die off until the desired ratio is reestablished. This can also serve as a containment mechanism to ensure that the bacteria in the consortium are not invasive to the environment outside the system. If any bacteria escape into the environment, the toxin produced by the bacteria will kill off the bacteria without the appropriate antitoxin present. In a particular example, one member of the consortium can produce the toxin ccdB. The production of the antitoxin ccdA can be activated by a quorum signal molecule from another member of the consortium. More detail about the use of quorum sensing molecules is available in the article: McCarty, Nicholas S. and Ledesma-Amaro, Rodrigo. Synthetic Biology Tools to Engineer Microbial Communities for Biotechnology. Trends in Biotechnology. February 2019, volume 37, issue 2, 181-197.

After sulfuric acid has been produced by the colony of sulfur-oxidizing bacteria, the sulfuric acid can be brought into contact with manganese. The sulfuric acid and manganese can react to yield hydrogen gas ($H_2$) and manganese sulfate ($MnSO_4$). The manganese sulfate can dissolve in water, and thus the manganese can react with the sulfuric acid and dissolve away. The hydrogen gas can be captured and the water containing the dissolved manganese sulfate can be disposed of, such as by pumping the water back into the body of water from which it originated.

Any source of manganese can be used to react with sulfuric acid and generate hydrogen gas. Manganese nodules represent a large potential resource of manganese on the seafloor. Manganese nodules are sometimes referred to as polymetallic nodules. These concretions of minerals often include multiple layers of iron and manganese hydroxides that form over millions of years. Small amounts of other metals can often be found in manganese nodules as well. Some materials that can be included in manganese nodules, in addition to manganese, include iron, silicon, aluminum, nickel, copper, cobalt, calcium, sodium, magnesium, potassium, titanium, barium, and others. Manganese nodules can vary in size from microscopic particles to multiple inches in diameter, with some being 8 or more inches in diameter. The nodules can be found in large numbers in certain areas of the seafloor in various locations throughout the oceans of the world. Many manganese nodules can be easily accessed on the seafloor, as they are often partially exposed above loose sand on the seafloor.

The methods of generating hydrogen gas described herein can include bringing the sulfuric acid produced by the colony of sulfur-oxidizing bacteria into contact with a manganese nodule so that the sulfuric acid reacts with the manganese nodule. The amount of sulfuric acid that is consumed in this reaction can depend on the amount manganese that is available. A manganese nodule can react with a sufficiently concentrated solution of sulfuric acid. In some examples, the manganese nodule can be contacted with a sulfuric acid solution having a concentration of about 0.9 grams sulfuric acid per liter of seawater, or a higher concentration. In some examples, the concentration can be from about 0.9 grams per liter to about 2 grams per liter. The manganese in the manganese nodule can react to produce one molecule of manganese sulfate and one molecule of hydrogen gas per atom of manganese and molecule of sulfuric acid that react. In some examples, the manganese nodule and the sulfuric acid can be held in a contained volume such as a reaction chamber while the reaction takes place and hydrogen gas is collected. In other examples, the manganese nodule can be held in a reaction chamber and a stream of sulfuric acid diluted with water can flow into the reaction chamber to provide a continuous supply of sulfuric acid to react with the manganese over time. A semi-continuous supply of manganese can also be provided by adding more manganese nodules to the chamber.

The methods of generating hydrogen gas described herein can be performed using any suitable equipment, devices, structures, and so on. As mentioned above, the method can be performed at a location that is submerged in a body of water, such as at or near the seafloor. Therefore, in some cases it can be useful to perform the method using equipment that is submerged in the body of water. The following description describes figures depicting example systems for generating hydrogen gas. In some examples, any of the systems described herein can be used to perform the methods of generating hydrogen gas. It is also noted that any features of the methods described herein can be performed by the systems described herein, and any features of the systems described herein can also be incorporated into the methods described herein.

Figure 3:
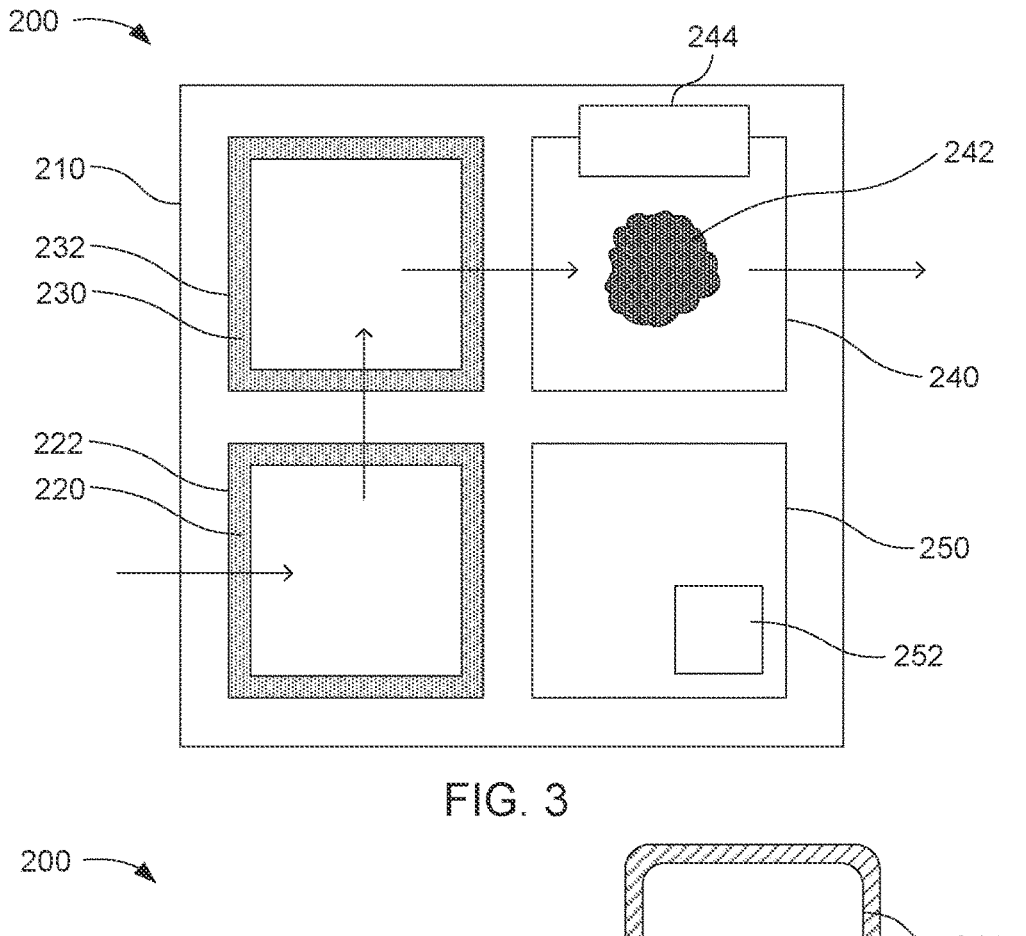
FIG. 3 is a schematic view of a system for generating hydrogen gas in accordance with still another example of the present invention.

FIG. 3 is a schematic illustration of an example system 200 for generating hydrogen gas. This system includes a housing 210 that can be submerged in a body of water. A colony of sulfur-reducing bacteria 220 is in the housing. These bacteria can convert sulfates to hydrogen sulfide as described above. In this particular example, the colony of sulfur-reducing bacteria is in the form of a film on the interior surface of a sulfur-reducing compartment 222, which is a compartment of the housing. A colony of sulfur-oxidizing bacteria 230 is also in the housing. These bacteria can convert hydrogen sulfide to sulfuric acid as described above. The colony of sulfur-oxidizing bacteria is in the form of a film on the interior surface of a sulfur-oxidizing compartment 232. A reaction chamber 240 is also included in the housing. The reaction chamber can hold a manganese nodule 242 as shown in the figure. Sulfuric acid produced by the colony of sulfur-oxidizing bacteria can react with the manganese nodule in this reaction chamber. In this example, a gas collector 244 is positioned in the reaction chamber to collect hydrogen gas produced by the reaction. The flow of water through the system is represented by arrows 246. Water first flows from the body of water into the sulfur-reducing compartment. Water and hydrogen sulfide flow from the sulfur-reducing compartment into the sulfur-oxidizing compartment. Water and sulfuric acid flow from the sulfur-oxidizing compartment into the reaction compartment. After the sulfuric acid reacts with the manganese nodule to generate hydrogen gas and manganese sulfate, the water and dissolved manganese sulfate flow back out from the reaction compartment into the body of water. This example system also includes a robotic collector 250 that can be used to collect manganese nodules from the seafloor and place the manganese nodules in the reaction chamber. The robotic collector includes an optical sensor 252 that can be used to detect manganese nodules on the seafloor. In some examples, the manganese nodules can be detected based on characteristics of the manganese nodules, such as size, shape, orientation, texture, cluster density, or a combination thereof.

Figure 4:
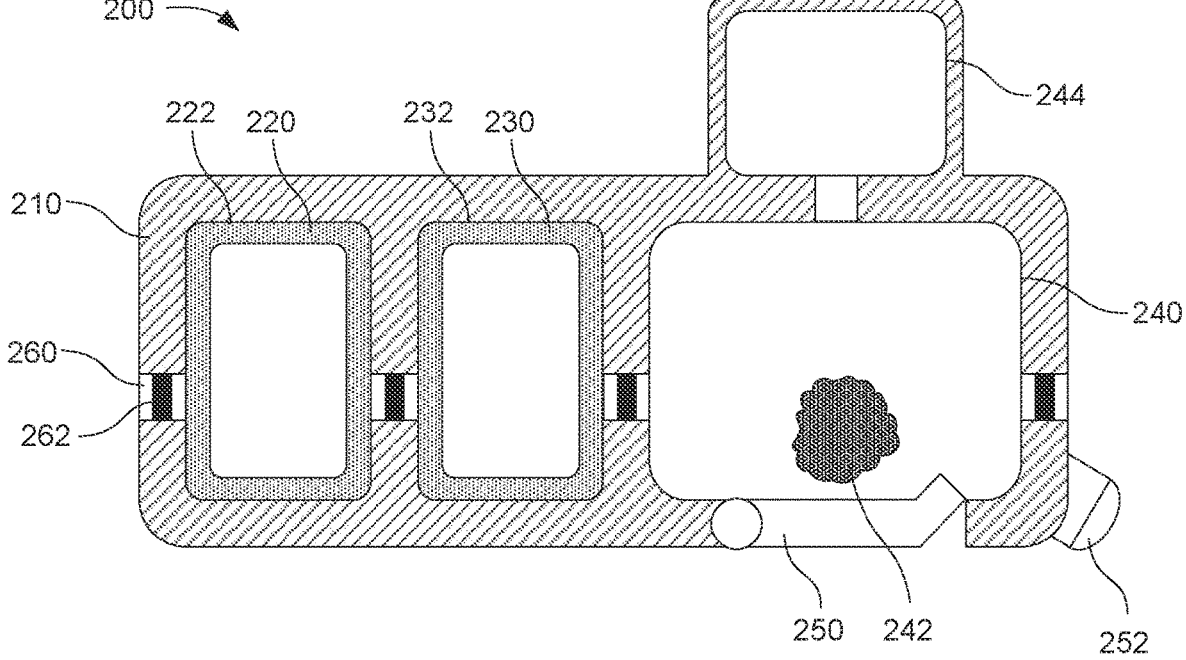
FIG. 4 is a cross-sectional view of another system for generating hydrogen gas in accordance with an example of the present invention.

FIG. 4 shows a cross-sectional view of a more detailed example system 200 for generating hydrogen gas. This example includes a housing 210 that can be submerged in a body of water. The housing includes a sulfur-reducing compartment 222 with a colony of sulfur-reducing bacteria 220 on an interior surface of the compartment. Water from the body of water can flow into the sulfur-reducing compartment through a water conduit 260. The water conduit in this example also includes a filter 262 that can allow water to pass through while preventing sand or other solid materials from entering the housing. The housing also includes a sulfur-oxidizing compartment 232 with a colony of sulfur-oxidizing bacteria 230 on an interior surface of that compartment. The sulfur-reducing bacteria can produce hydrogen sulfide in the sulfur-reducing compartment and then water and the hydrogen sulfide can flow from the sulfur-reducing compartment into the sulfur-oxidizing compartment through another water conduit. The hydrogen sulfide can then be converted into sulfuric acid by the sulfur-oxidizing bacteria. The sulfuric acid and water can flow through another water conduit into a reaction chamber 240 holding a manganese nodule. The sulfuric acid can react with the manganese to generate hydrogen gas, which can be collected by a gas collector 244. In this case, the gas collector is a gas storage tank located above the reaction chamber. A robotic collector 250 in the form of a scoop is on the bottom of the housing. The scoop can open to pick up a manganese nodule off the seafloor and then close to enclose the manganese nodule inside the reaction chamber. The system also includes an optical sensor 252 that can be used to optically find and identify manganese nodules to be collected using the scoop. Manganese sulfate can be produced as a byproduct of the hydrogen generation reaction. This manganese sulfate and the water in the reaction chamber can be exhausted through another water conduit back into the body of water (i.e., the ocean).

In the example of FIG. 4, filters 262 are placed in each of the water conduits 260. These filters can prevent the unwanted movement of solid materials through the water conduits. In some examples it may be desired to contain the bacteria in the separate bacterial colonies so that the bacteria do not intermix between the colonies. In such examples, the filters can be designed to prevent solids the size of bacterial cells from passing through. However, the filters can be designed to allow chemical compounds of interest such as hydrogen sulfide and sulfuric acid to pass through. In other examples, if separating the bacteria is not an issue, then the filters can be designed to admit solids the size of cells while prevent larger particles, such as sand, from passing through the filters. It is noted that such filters can be used in some examples, while other examples may not include any filters. Additionally, filters can be included in certain locations and omitted in others. For example, filters can be included in a water inlet into the housing and an outlet out of the housing, but may be omitted in water conduits connected the compartments within the housing.

In some examples, the pH in the sulfur-reducing compartment can be different from the pH in the sulfur-oxidizing compartment. For example, the pH in the sulfur-reducing compartment can be from about 6 to about 8, and the pH in the sulfur-oxidizing compartment can be from about 3 to about 4. In further examples, the various bacteria used in the system can also be split into additional compartments. For example, the neutrophilic sulfur-oxidizing bacteria can be present in a separate compartment from the acidophilic sulfur-oxidizing bacteria. The pH in these compartments can also be different.

The examples shown in FIGS. 3 and 4 are merely two examples of system designs that can be made in accordance with the present disclosure. Systems for generating hydrogen gas can be made with a wide variety of other designs, including bacterial colonies, compartments, conduits, housings, robotic collectors, and other components that can have a different shape and arrangement than shown in the figures. In some examples, the colonies of bacteria can be in the form of a film on an interior surface of a compartment in the housing, as shown in the above figures. However, the colonies can also have other arrangements. For example, the bacteria can grow on a portion of the housing that is not enclosed in a compartment. In some examples, colonies of bacteria can be in the form of a film growing on the housing in an area that is open to the body of water. Thus, in various examples, the colonies can be in or on the housing. In further examples, the bacteria can grow on a solid growth structure or media inside a compartment. For example, a compartment in the housing can be filled with beads or a porous lattice or some other solid structure. In some examples, the solid structure or media can have an increased surface area compared to the interior surface of the compartment itself. This can provide more area for bacterial colonies to grow. In still further examples, the bacterial colonies can be in the form of free-floating individual bacteria or bacteria that conglomerate in floating films that are not attached to a solid surface.

The reaction chamber can be at least partially enclosed by the housing. This can allow diluted sulfuric acid to be contained in the same volume with the manganese nodule for a sufficient time to react with the manganese nodule. The housing can also at least partially enclose the reaction chamber in such a way that hydrogen gas can be captured by the housing. In certain examples, the housing can completely enclose the reaction chamber with exceptions including inlets and outlets for water, manganese nodules, hydrogen gas, and any other materials that are to be let in or out of the reaction chamber.

In some examples, the system can include a gas collector to collect the hydrogen gas. The gas collector can be a part of the housing or a component positioned inside the reaction chamber to capture hydrogen gas generated by the reaction of sulfuric acid with the manganese nodule. For example, the gas collector can include a hood or container that is open at a bottom end, which is positioned above the manganese nodule so that hydrogen gas bubbles can rise from the manganese nodule into the hood or container. The gas collector can also include a storage tank for the hydrogen gas if the hydrogen is to be stored, or a hydrogen line leading to a hydrogen fuel cell, or a hydrogen line leading to a connector for transferring hydrogen out of the system for some other use, or a combination thereof. Accordingly, in some examples the hydrogen can be stored and in other examples the hydrogen can be used immediately for electricity generation in a hydrogen fuel cell or for some other purpose.

As mentioned above, manganese nodules can be collected using a robotic collector. The robotic collector can take a variety of forms and include a variety of features and components. In some examples, the robotic collector can be a part of the system that is integrated in a housing with the other parts of the system, including the colonies of bacteria and reaction chamber. The example shown in FIG. 4 has such a robotic collector, which includes a scoop that can open downwardly from the housing to scoop up manganese nodules off the seafloor. Other mechanisms for collecting the manganese nodules can also be used, such as a robotic claw mechanism, a vacuum suction mechanism, a sieve for separating manganese nodules from sand, and others. In alternative examples, the robotic collector can be a separate unmanned underwater vehicle that can move independently to find and collect manganese nodules. This separate robotic collector can then bring the manganese nodules to the system and place the nodules in the reaction chamber.

The robotic collector can be autonomous, or remotely controlled, or a combination thereof. The robotic collector can also include an optical sensor to help find and identify manganese nodules. Whether the robotic collector is autonomous or remotely controlled, in some examples the optical sensor can be used to detect manganese nodules based on a characteristic such as size, shape, orientation, texture, cluster density, or a combination thereof. The robotic collector can also include additional sensors such as a weight sensor, magnetic sensor, sonar, or other sensors that can measure other properties of manganese nodules to help detect manganese nodules. For autonomous robotic collectors, in some examples the robotic collector can include a processor running software that has been trained using machine learning to recognize manganese nodules. The machine learning can include the use of previously obtained photographs of manganese nodules on the seafloor, or data obtained using the robotic collector itself to gather manganese nodules from the seafloor, or a combination thereof. In one example, a set of training images can include photographs of the seafloor that contain manganese nodules and photographs of the seafloor that do not contain manganese nodules. The images can be labeled as either containing manganese nodules or not containing manganese nodules, and a machine learning algorithm can be trained to recognize images containing manganese nodules.

Systems and Methods of Separating Oxygen from a Body of Water

The present disclosure also describes systems and methods of separating oxygen from a body of water. As mentioned above, oxygen can be combined with hydrogen in a hydrogen fuel cell to generate electrical power. Accordingly, the oxygen produced by these systems and methods can be used for electricity generation in some examples. In other examples, the oxygen can be used for any other purpose, such as replenishing oxygen of diving tanks or manned underwater vehicles.

Figure 5:
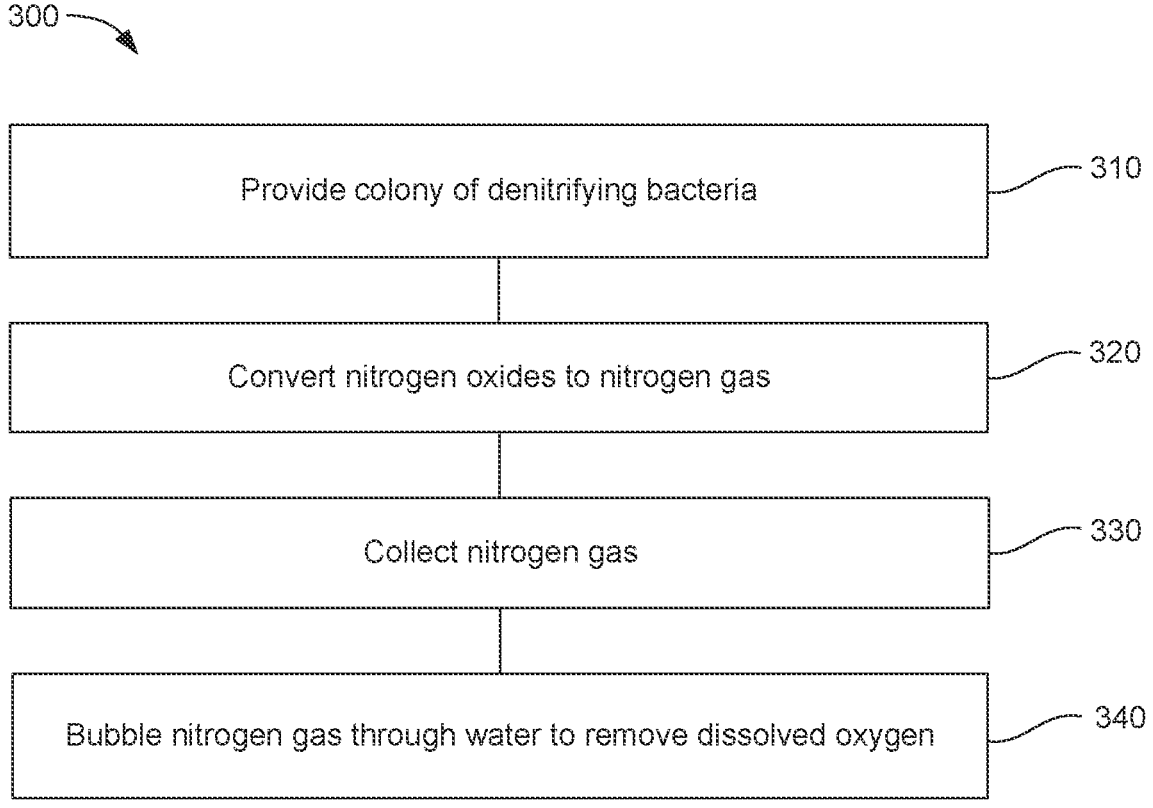
FIG. 5 is a flowchart illustrating a method of separating oxygen from a body of water in accordance with an example of the present invention.

An example method 300 of separating oxygen from a body of water is shown in FIG. 5. The method includes providing a colony of denitrifying bacteria 310; converting nitrogen oxides to nitrogen gas 320; collecting the nitrogen gas 330; and bubbling the nitrogen gas through water to remove dissolved oxygen 340.

The methods of separating oxygen from a body of water can be performed at a location that is submerged in the body of water. Nitrogen oxides, such as nitrite and nitrate, are naturally found in the ocean and other bodies of water at a variety of depths. Dissolved oxygen is also naturally found in seawater and other bodies of water. Therefore, the raw materials used in these methods can be obtained from seawater or from another body of water. In certain examples, the method of separating oxygen can be performed in an ocean at a depth within about 10 meters of the seafloor, or within about 5 meters of the seafloor, or within about 1 meter of the seafloor. However, since nitrates are typically found throughout a wide depth range in the ocean, the method can be performed at other depths as well. In certain examples, the colony of denitrifying bacteria can be in or on a housing that is submerged in the ocean or other body of water. In certain examples, the housing can be submerged within 10 meters of the seafloor, or resting directly on the seafloor. The housing can be part of an underwater unmanned vehicle that can be resting on the seafloor, freely floating near the seafloor, or tethered to the seafloor.

Figure 6:
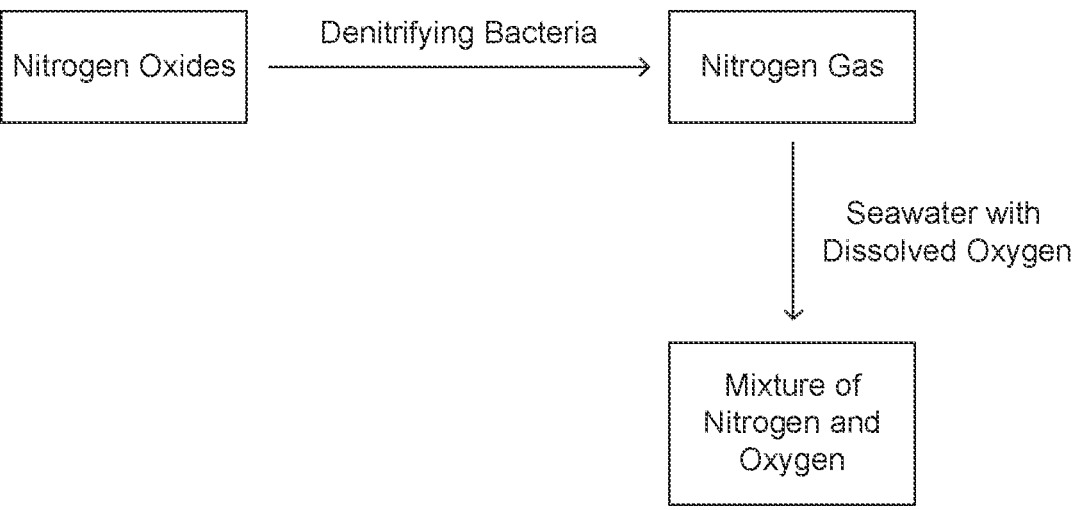
FIG. 6 is a reaction scheme showing a process of separating oxygen from a body of water in accordance with another example of the present invention.

FIG. 6 is a reaction scheme showing a process of separating oxygen from seawater. Nitrogen oxides, such as nitrate or nitrite, are the starting material in the process. The nitrogen oxides are converted to nitrogen gas by denitrifying bacteria. The nitrogen gas is then bubbled through seawater containing dissolved oxygen. The nitrogen extracts the oxygen from the seawater, forming a mixture of nitrogen and oxygen.

In some examples, the conversion of nitrogen oxides into nitrogen gas and the bubbling of the nitrogen gas through water to extract dissolved oxygen can be occur in sequence. For example, a certain quantity of water from the body of water can be brought into contact with a colony of denitrifying bacteria. The denitrifying bacteria can convert nitrates and/or nitrites in the water into nitrogen gas. The nitrogen gas that is produced in this way can be collected over time until a desired amount of nitrogen gas has been collected. Then, the nitrogen gas can be bubbled through another portion of water taken from the body of water to remove dissolved oxygen from the water. In some examples, multiple of these batches can be processed simultaneously. For example, a batch of water containing nitrogen oxides can be processed using the colony of denitrifying bacteria to produce nitrogen. At the same time, nitrogen gas that was produced from a previous batch can be bubbled through a separate portion of water from the body of water to remove oxygen from the water. Thus, multiple batches can be run in parallel.

In other examples, the conversion of nitrogen oxides to nitrogen gas and the bubbling of the nitrogen gas through water can occur simultaneously. For example, as the nitrogen gas is produced by the colony of denitrifying bacteria, the nitrogen gas can be collected and directed to flow through another portion of water while the denitrification is still in progress. Alternatively, the nitrogen gas can extract oxygen from the same water where the colony of denitrifying bacteria is located and then the mixture of nitrogen and oxygen gas can be collected. In further examples, a hybrid of batch and continuous-type processes can be used, in which one stage of the process is run as a batch and another stage is run continuously.

In more detail regarding the bacteria used in the method of separating oxygen from the body of water, the method can involve at least a colony of denitrifying bacteria. These can include bacteria capable of converting nitrogen oxides (including nitrate $NO_3^+$ and nitrite $NO_2^-$ ions) into nitrogen gas $(N_2)$. In some examples, a colony of ammonia nitrifying bacteria and/or a colony of nitrite-oxidizing bacteria can also be used. These can convert ammonia into nitrite and nitrite into nitrate, respectively.

A variety of denitrifying bacteria exist that can convert nitrate into nitrogen gas. Such bacteria have been used for removing nitrogen compounds from industrial waste streams. In some examples, the denitrifying bacteria can be aerobic bacteria that produce nitrogen from nitrates through an aerobic denitrification pathway. One example pathway involves first converting nitrate to nitrite using a nitrate reductase enzyme; then converting the nitrite to nitric oxide (NO) using a nitrite reductase enzyme; then converting the nitric oxide to nitrous oxide $(N_2O)$ using a nitric oxide reductase enzyme; and then converting the nitrous oxide to nitrogen gas $(N_2)$ using a nitrous oxide reductase enzyme. One example type of bacteria that can perform this pathway is *Pseudomonas*. This bacteria has been isolated in a wide variety of environments, including coastal sediments and deep in the Marianas Trench. Thus, *Pseudomonas* is capable of surviving and growing in a variety of conditions. Certain strains of *Pseudomonas* have been experimentally tested for nitrogen production. *Pseudomonas stutzeri* strain YG-24 has been found to produce 100 mg of nitrogen gas in 20 hours from one liter of a 2 millimolar nitrate solution. When grown in a 5 millimolar nitrate solution, *Pseudomonas stutzeri* was able to produce 85.6 nanomoles (5.3 milligrams) of nitrogen gas per minute per milligram of dry bacteria weight. In a 5 millimolar nitrate solution, *Pseudomonas aeruginosa* was able to produce 287.8 nanomoles (17.7 milligrams) of nitrogen gas per minute per milligram of dry bacteria weight. Thus, different strains can produce nitrogen at different rates. The rate of nitrogen production in the methods described herein can depend on the strain of denitrifying bacteria used, the concentration of nitrate available in the environment, the amount of water processed, and the amount of bacteria present.

In further examples, a colony of ammonia nitrifying bacteria and/or a colony of nitrite-oxidizing bacteria can also be used in the method. These can help to produce more nitrogen gas by converting ammonia from the body of water into nitrite and then into nitrate. The nitrate can then be converted to nitrogen using the denitrifying bacteria. Examples of ammonia nitrifying bacteria include *Nitrosomonas, Nitrococcus, Nitrosospira*, and combinations thereof. Examples of nitrite-oxidizing bacteria include *Nitrobacter, Nitrospina, Nitrococcus, Nitrospira*, and combinations thereof.

In some examples, a consortium of multiple types of bacteria can be used in the methods of separating oxygen from a body of water. The colony of denitrifying bacteria mentioned above can be a consortium, and/or the colony of denitrifying bacteria can be a part of a larger consortium of multiple types of bacteria. In certain examples, the consortium can include a denitrifying bacteria, an ammonia-nitrifying bacteria, a nitrite-oxidizing bacteria, or a combination thereof. Additionally, any of the consortium design tools and techniques described above with respect to the bacteria used in the systems and methods of generating hydrogen gas can also be used in the systems and methods of separating oxygen from a body of water. For example, the metabolic pathways used to convert nitrates to nitrogen gas can be split into smaller parts and the parts can be spread across multiple bacteria in the consortium. The consortium can also include natural bacteria, engineered bacteria, or a combination thereof as explained above. The consortium can also be designed to produce quorum sensing molecules, toxin/anti-toxins systems, or combinations thereof as described above.

After a desired amount of nitrogen gas has been produced, or simultaneous with the production of nitrogen gas, the nitrogen gas can be collected and bubbled through a portion of water from the body of water to remove dissolved oxygen from the portion of water. In some examples, the nitrogen gas can be bubbled through the water using a bubble diffuser. The bubble diffuser can be a device having many small holes or pores, or a gas-permeable material, configured to release many small bubbles of nitrogen gas into the water. Bubbling nitrogen through water in this way is also referred to as sparging, and equipment designed for sparging can be used to bubble the nitrogen gas through the water. Dissolved oxygen in the water can diffuse out of the liquid phase into the gas bubbles. The bubbles can then be collected by a gas collector as a mixture of nitrogen and oxygen.

In some examples, the mixture of nitrogen and oxygen can be recycled and bubbled through the water again to remove more oxygen, or the gas mixture can be bubbled through a different volume of water to remove oxygen from that volume of water. Alternatively, nitrogen gas can be bubble through water once and collected without recycling the gas.

In further examples, the desired amount of oxygen can be separated from a single batch of water taken from the body of water. For example, a compartment or tank can be filled with water and the nitrogen gas can be bubbled through the water until a desired amount of oxygen is obtained. In other examples, the water can be replaced with fresh water one or more times. Thus, nitrogen gas can be bubbled through one batch of water for a period of time until some or all of the oxygen has been removed from the water, and then the water can be replaced by a new volume of water that has more dissolved oxygen. Nitrogen bubbling has been used in laboratories for the purpose of removing substantially all oxygen from water to provide sterile water without any oxygen content. However, in the methods described herein, there is no need to produce water with an oxygen content of zero. Instead, nitrogen can be bubble through water until a portion of the dissolved oxygen has been removed, such as 20%, 40%, 50%, 60%, or 80% of the initial dissolved oxygen. The water can then be replaced with a fresh volume of water. Since the last 20% or 10% of oxygen dissolved in water can be the most difficult to remove, this can allow for obtaining oxygen more quickly in the methods described herein compared to laboratory methods of producing sterile oxygen-free water.

The mixture of nitrogen and oxygen gas can be used for a variety of purposes. As mentioned above, the gas mixture can be used to provide oxygen to a hydrogen fuel cell to generate electricity. The gas mixture can also be used as breathable air for manned underwater vehicles. In certain examples, the gas mixture can be used without separating the oxygen from the nitrogen. However, in other examples the method can include separating the oxygen from the nitrogen to obtain oxygen gas at a higher concentration or pure oxygen gas. Separation methods can include allowing the oxygen to settle out of the nitrogen in a settling tank, or cryogenic separation, or distillation, or centrifuge separation, zeolite bed adsorber separation, or others.

The methods of separating oxygen from a body of water described herein can be performed using any suitable equipment, devices, structures, and so on. As mentioned above, the method can be performed at a location that is submerged in a body of water, such as at or near the seafloor. Therefore, in some cases it can be useful to perform the method using equipment that is submerged in the body of water. The following description describes figures depicting example systems for separating oxygen from a body of water. In some examples, any of the systems described herein can be used to perform the methods of separating oxygen from the body of water. It is also noted that any features of the methods described herein can be performed by the systems described herein, and any features of the systems described herein can also be incorporated into the methods described herein.

Figure 7:
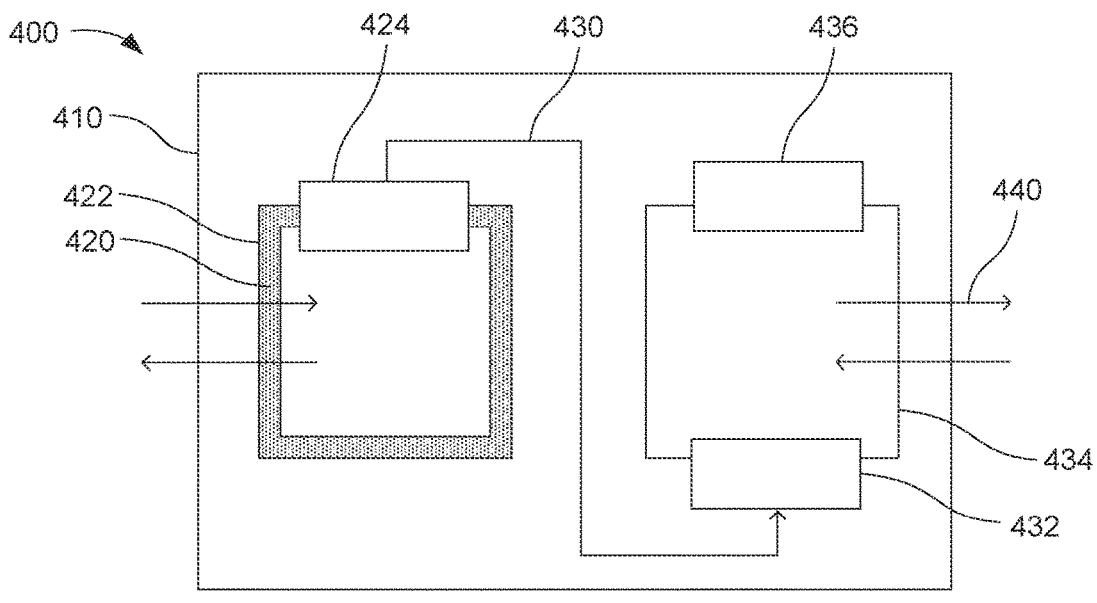
FIG. 7 is a schematic view of a system for separating oxygen from a body of water in accordance with yet another example of the present invention.

FIG. 7 is a schematic illustration of an example system 400 for separating oxygen from a body of water. The system includes a housing 410 that can be submerged in a body of water. A colony of denitrifying bacteria 420 is in the housing. In this example, the colony of denitrifying bacteria is in the form of a film on an interior surface of a denitrifying compartment 422, which a compartment of the housing. A nitrogen collector 424 is positioned in an upper portion of the denitrifying compartment to collect the nitrogen gas produced by the colony of denitrifying bacteria. The nitrogen gas flows through nitrogen line 430 to a bubble diffuser 432. The bubble diffuser is positioned in a lower portion of a bubbling compartment 434. In this compartment, the nitrogen gas can bubble through water taken from the body of water to remove dissolved oxygen from the water. A mixture of nitrogen and oxygen gas can be collected by a gas collector 436 at an upper portion of the bubbling compartment. Arrows 440 represent the flow of water into and out of the housing. Water can flow from the body of water into the denitrifying compartment so that the colony of denitrifying bacteria can convert nitrates in the water into nitrogen gas. Water can also flow separately from the body of water into the bubbling compartment so that nitrogen gas can be bubbled through the water to remove dissolved oxygen from the water.

Figure 8:
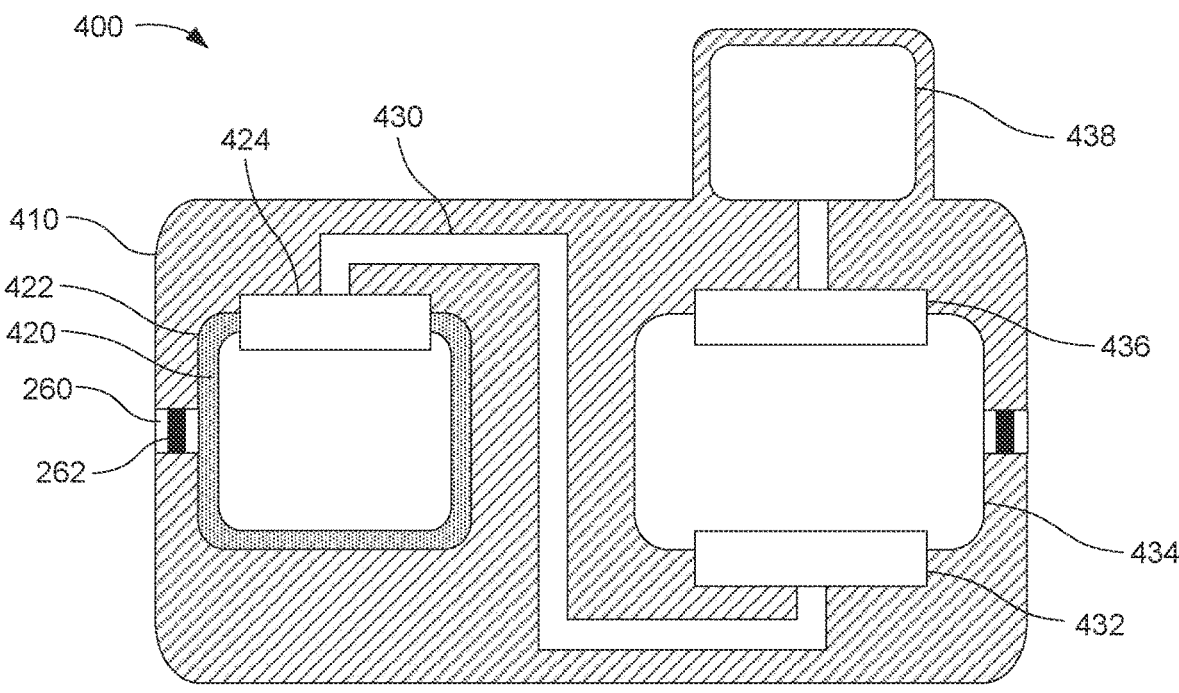
FIG. 8 is a cross-sectional view of a system for separating oxygen from a body of water in accordance with still another example of the present invention.

FIG. 8 shows a cross-sectional view of a more detailed example system 400 for separating oxygen from a body of water. This example includes a housing 410 that can be submerged in a body of water. The housing includes a denitrifying compartment 422 with a colony of denitrifying bacteria 420 on an interior surface of the compartment. A nitrogen collector 424 is positioned in an upper portion of the denitrifying compartment to collect nitrogen gas. Water from the body of water can flow into the denitrifying compartment through a water conduit 260. The water conduit in this example also includes a filter 262 that can allow water to pass through while preventing sand or other solids from entering the housing. In certain examples, the filter can also prevent foreign bacteria from entering the denitrifying compartment, and also prevent the denitrifying bacteria from escaping from the compartment. The housing also includes a bubbling compartment 434. A bubble diffuser 432 is positioned in a lower portion of the bubbling compartment. Nitrogen gas can flow from the nitrogen collector to the bubble diffuser through a nitrogen line 430. The nitrogen gas can bubble up from the bubble diffuser through water in the bubbling compartment. Dissolved oxygen can migrate from the water to the gas bubbles, forming a mixture of nitrogen and oxygen gas. The bubbles can then be collected by a gas collector 436 at an upper portion of the bubbling compartment. In this example, the gas collector is connected to a gas storage tank 438 where the mixture of nitrogen and oxygen can be stored. Water can flow into and out of the bubbling compartment through another water conduit and filter.

The water conduits and filters can have same features as described above in the systems for generating hydrogen gas. The housing can also be designed having any of the features described above in the systems for generating hydrogen gas. It is noted that any of the systems described herein can include additional components that are useful for operation but which may not be shown in the figures. For example, the systems can include pumps and/or valves for directing the flow water through various water conduits in the systems.

Systems and Methods of Generating Electricity in a Body of Water

The present disclosure also describes systems and methods of generating electricity in a body of water. These systems and methods can include combining hydrogen and oxygen in a hydrogen fuel cell to generate electricity. In some examples, the hydrogen can be generated by a system or method of generating hydrogen as described above. The oxygen can be obtained by a system or method of separating oxygen from a body of water as described above. Accordingly, in some examples, the systems and methods of generating electricity in a body of water can include a combination of the systems and methods described above.

FIG. 9 is a flowchart illustrating an example method 500 of generating electricity in a body of water. The method includes: providing colonies of sulfur-reducing bacteria, sulfur-oxidizing bacteria, and denitrifying bacteria 510; converting sulfates to hydrogen sulfide 520; converting hydrogen sulfide to sulfuric acid 530; reacting the sulfuric acid with manganese to produce hydrogen gas 540; converting nitrogen oxides to nitrogen gas 550; bubbling the nitrogen gas through water to remove dissolved oxygen 560; and combining the hydrogen gas and oxygen gas in a fuel cell generator to generate electricity 570.

Figure 10:
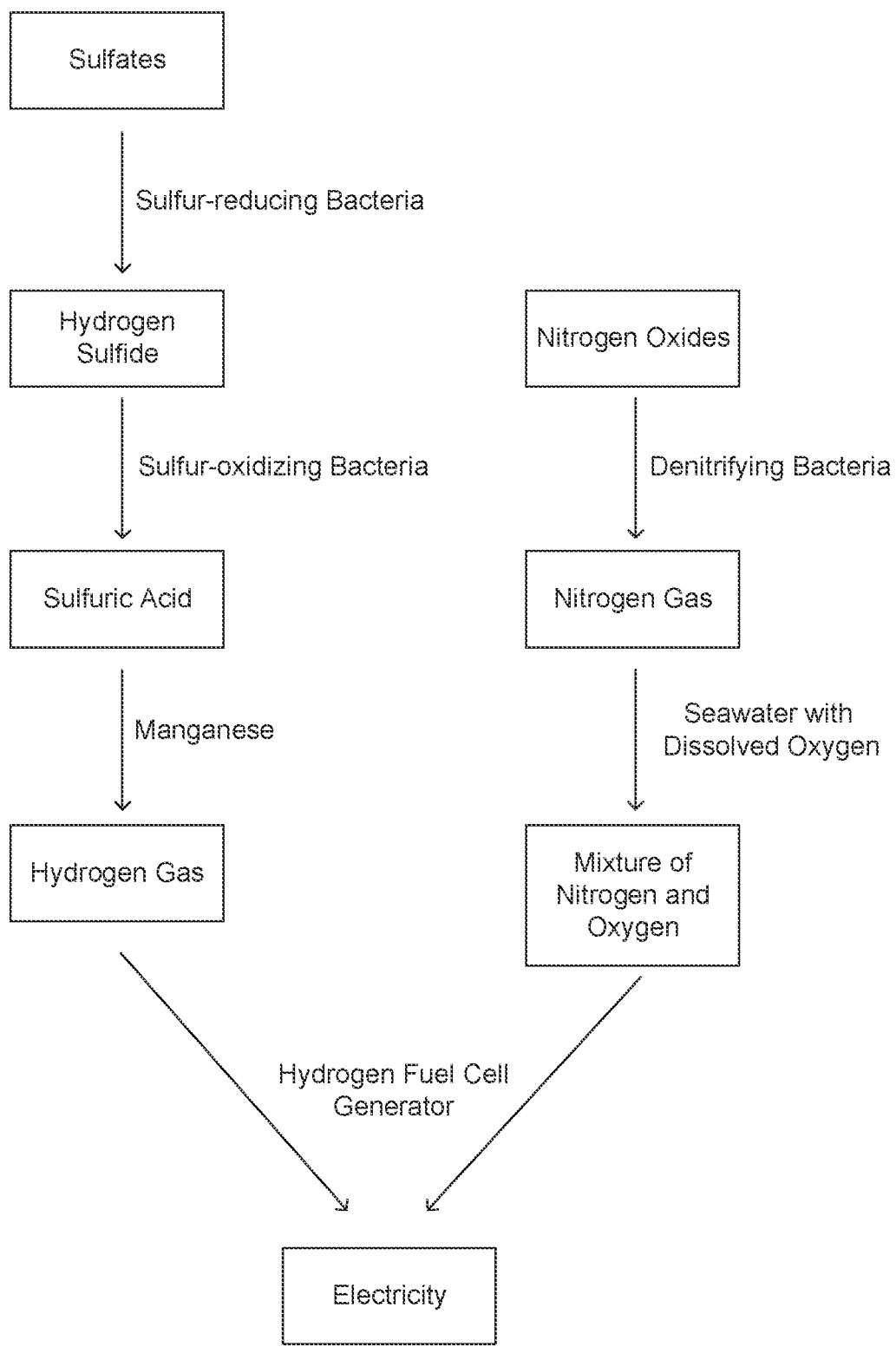
FIG. 10 is a reaction scheme showing a process of generating electricity in a body of water in accordance with an example of the present invention.

FIG. 10 is a reaction scheme showing a simplified process for generating electricity in a body of water. The process includes two branches: one for generating hydrogen gas, and one for separating oxygen gas from the body of water. In the first branch, sulfates are reduced by sulfur-reducing bacteria to produce hydrogen sulfide. The hydrogen sulfide is then oxidized by sulfur-oxidizing bacteria to produce sulfuric acid. The sulfuric acid reacts with manganese to produce hydrogen gas. In the second branch, nitrogen oxides are converted to nitrogen gas by denitrifying bacteria. The nitrogen gas is then used to remove dissolved oxygen from seawater to produce a mixture of nitrogen and oxygen. After the process of both branches is complete, the hydrogen gas and oxygen gas are combined in a hydrogen fuel cell generator to generate electricity.

In various examples, the hydrogen gas and oxygen gas that are combined in the hydrogen fuel cell can be obtained using the methods of generating hydrogen and methods of separating oxygen from a body of water as describe above. Thus, any of the processes and features described above can be used to prepare the hydrogen gas and oxygen gas for use in the fuel cell. In some examples, the entire method of generating electricity can be performed at a location submerged in a body of water. In certain examples, the location can be submerged in an ocean at a depth within about 10 meters of the seafloor, or within about 5 meters of the seafloor, or within about 1 meter of the seafloor. The method can be performed using a system that is submerged at these depths. The system can also be resting directly on the seafloor, or freely floating near the seafloor, or tethered to the seafloor. Accordingly, the methods and systems can be used to provide electricity at a depth near the seafloor.

The hydrogen fuel cell used to generate electricity can be any suitable type of hydrogen fuel that can be powered by hydrogen gas and oxygen gas. As mentioned above, in some examples the oxygen gas can be mixed with nitrogen gas and this gas mixture can be used directly with the hydrogen fuel cell when generating electricity. In other examples, the oxygen can be concentrated to provide a higher oxygen concentration, or the oxygen can be fully separate from the nitrogen to provide pure oxygen for use with the hydrogen fuel cell. Some examples of hydrogen fuel cell designs that can be used include proton-exchange membrane fuel cells, phosphoric acid fuel cells, solid acid fuel cells, alkaline fuel cells, solid oxide fuel cells, molten carbonate fuel cells, and others.

Figure 11:
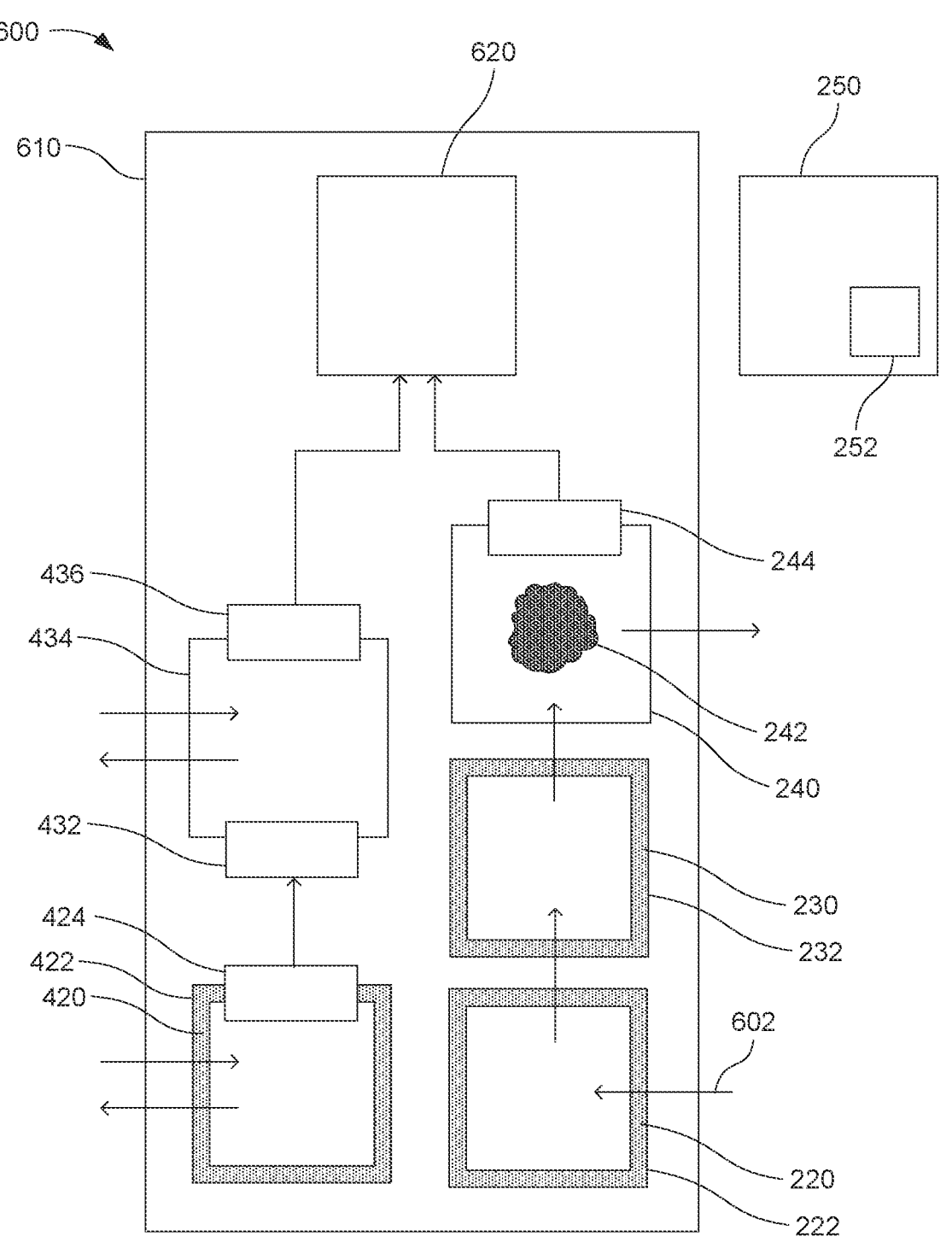
FIG. 11 is a schematic view of a system for generating electricity in a body of water in accordance with another example of the present invention.

FIG. 11 is a schematic illustration of an example system 600 for generating electricity in a body of water. The system includes a housing 610 that can be submerged in the body of water. Several compartments are formed in the housing. A sulfur-reducing compartment 222 contains a colony of sulfur-reducing bacteria 220. In this example, the colony of sulfur-reducing bacteria is in the form of a film on an interior surface of the sulfur-reducing compartment. The housing also includes a sulfur-oxidizing compartment 232 containing a colony of sulfur-oxidizing bacteria 230. The colony of sulfur-oxidizing bacteria is also in the form of a film on an interior surface of the sulfur-oxidizing compartment. A reaction chamber 240 is also included in the housing. The reaction chamber contains a manganese nodule 242 and a hydrogen gas collector 244.

In this figure, arrows 602 represent the flow of water into and between the compartments. In this example, water can flow from the body of water into the sulfur-reducing compartment 222. The water can contain naturally-occurring sulfates, which can be reduced by the colony of sulfur-reducing bacteria 220 to form hydrogen sulfide. The hydrogen sulfide and water can then flow into the sulfur-oxidizing compartment 232, where the colony of sulfur-oxidizing bacteria 230 can oxidize the hydrogen sulfide to form sulfuric acid. The sulfuric acid and water then flow into the reaction chamber 240 and the sulfuric acid reacts with the manganese nodule 242 to generate hydrogen gas. The hydrogen gas can be collected by the hydrogen gas collector 244 and water and byproducts can flow back out into the body of water.

The housing 610 also includes a denitrifying compartment 422 containing a colony of denitrifying bacteria 420. The colony of denitrifying bacteria is also in the form of a film on an interior surface of the denitrifying compartment. Water can flow into the denitrifying compartment from the body of water. Naturally-occurring nitrates or other nitrogen compounds can be converted to nitrogen gas by the colony of denitrifying bacteria. A nitrogen gas collector 424 in the denitrifying compartment can collect the nitrogen gas. The nitrogen gas then flows into a bubbling compartment 434 that contains a bubble diffuser 432 for producing many small bubbles of nitrogen gas. The bubbling compartment can contain a portion of water taken from the body of water, which contains dissolved oxygen. The nitrogen bubbles can remove dissolved oxygen from the water, forming a gas mixture of nitrogen and oxygen. The gas mixture can be collected by a gas collector 436 in an upper portion of the bubbling compartment. The oxygen/nitrogen mixture and the hydrogen gas can both flow to a hydrogen fuel cell generator 620 that can combine the oxygen and the hydrogen to generate electricity.

The system 600 in FIG. 11 also includes a robotic collector 250 with an optical sensor 252, as described above in the systems for generating hydrogen gas. In this example, the robotic collector is schematically shown as being separate from the housing 610 containing the rest of the system components. This illustrates that the robotic collector can be a separate device, such as a separate unmanned underwater vehicle that can move independently and collect manganese nodules from the seafloor. In other examples, the robotic collector can be integrated in the housing with the reset of the system. In some examples, the entire system can be an unmanned underwater vehicle that can move in the water to locate and collect manganese nodules, while the system can also collect seawater for the production of hydrogen and oxygen through the various bacterial colonies in the system.

Figure 12:
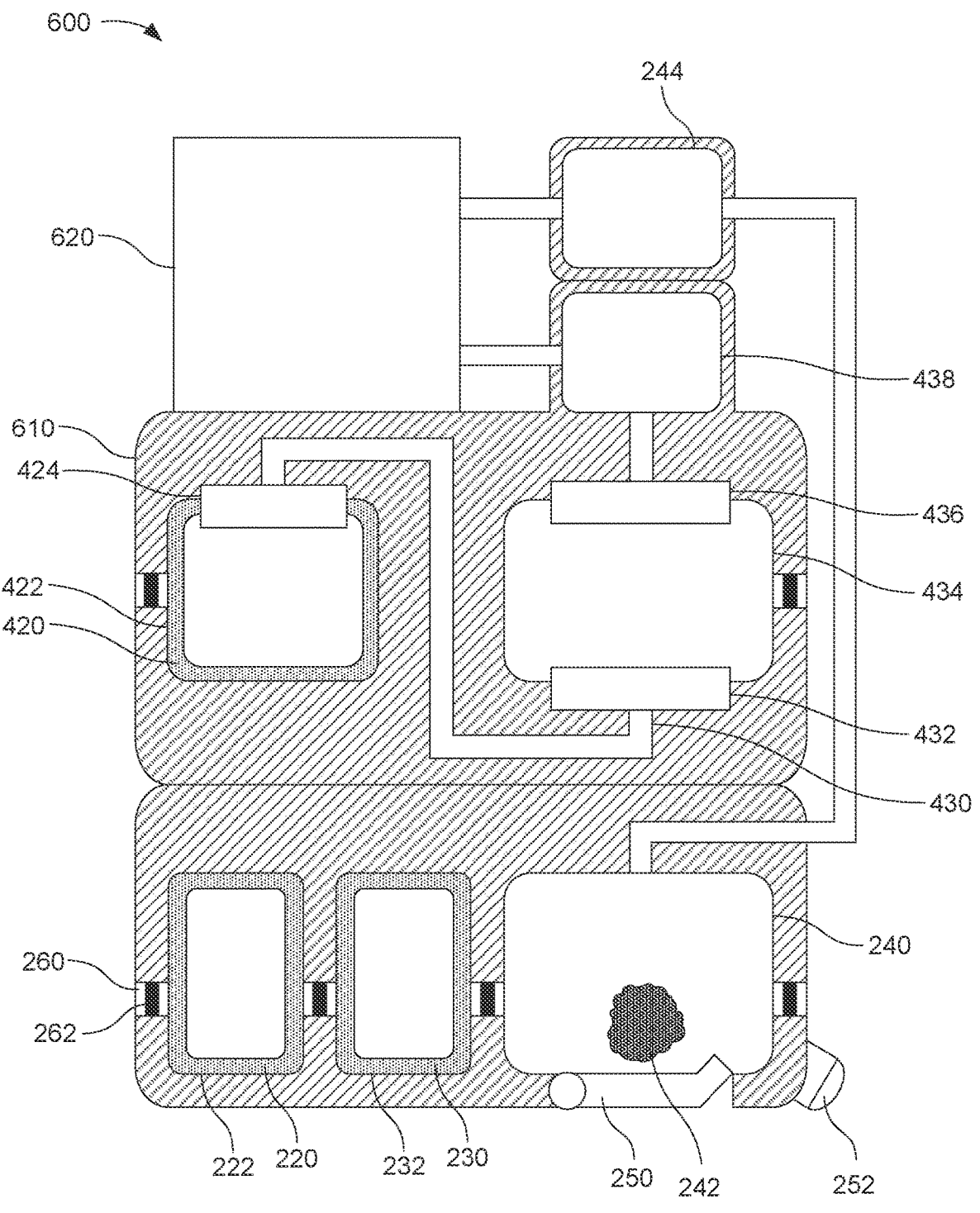
FIG. 12 is a cross-sectional view of a system for generating electricity in a body of water in accordance with yet another example of the present invention.

FIG. 12 shows a cross-sectional view of a more detailed example system 600 for generating electricity in a body of water. This example includes a housing 610 that can be submerged in a body of water. The housing includes a sulfur-reducing compartment 222 with a colony of sulfur-reducing bacteria 220 on an interior surface of the compartment. Water from the body of water can flow into the sulfur-reducing compartment through a water conduit 260. The water conduits in this example also include filters 262 that can allow water to pass through while preventing sand or other solid materials from entering the housing. The housing also includes a sulfur-oxidizing compartment 232 with a colony of sulfur-oxidizing bacteria 230 on an interior surface of that compartment. The sulfur-reducing bacteria can produce hydrogen sulfide in the sulfur-reducing compartment and then water and the hydrogen sulfide can flow from the sulfur-reducing compartment into the sulfur-oxidizing compartment through another water conduit. The hydrogen sulfide can then be converted into sulfuric acid by the sulfur-oxidizing bacteria. The sulfuric acid and water can flow through another water conduit into a reaction chamber 240 holding a manganese nodule 242. The sulfuric acid can react with the manganese to generate hydrogen gas, which can be collected by a gas collector 244. In this case, the gas collector is a hydrogen storage tank located at the top of the system. A robotic collector 250 in the form of a scoop is on the bottom of the housing. The scoop can open to pick up a manganese nodule off the seafloor and then close to enclose the manganese nodule inside the reaction chamber. The system also includes an optical sensor 252 that can be used to optically find and identify manganese nodules to be collected using the scoop. Manganese sulfate can be produced as a byproduct of the hydrogen generation reaction. This manganese sulfate and the water in the reaction chamber can be exhausted through another water conduit back into the body of water.

The system 600 also includes a denitrifying compartment 422 with a colony of denitrifying bacteria 420 on an interior surface of the compartment. A nitrogen collector 424 is positioned in an upper portion of the denitrifying compartment to collect nitrogen gas. Water from the body of water can flow into the denitrifying compartment through a water conduit 260, including another filter 262. The housing also includes a bubbling compartment 434. A bubble diffuser 432 is positioned in a lower portion of the bubbling compartment. Nitrogen gas can flow from the nitrogen collector to the bubble diffuser through a nitrogen line 430. The nitrogen gas can bubble up from the bubble diffuser through water in the bubbling compartment. Dissolved oxygen can migrate from the water to the gas bubbles, forming a mixture of nitrogen and oxygen gas. The bubbles can then be collected by a gas collector 436 at an upper portion of the bubbling compartment. In this example, the gas collector is connected to a gas storage tank 438 where the mixture of nitrogen and oxygen can be stored. Water can flow into and out of the bubbling compartment through another water conduit and filter.

Hydrogen gas from the hydrogen storage tank 244 and oxygen from the mixture of oxygen and nitrogen in the gas storage tank 438 can flow to a hydrogen fuel cell generator 620. The hydrogen fuel cell generator can combine the oxygen and hydrogen to produce electricity.

In some examples, the system can produce electricity to recharge batteries of other unmanned underwater vehicles. Thus, the system can act as a mobile charging station for other vehicles. As mentioned above, the system can be located at a depth near the seafloor, which can be convenient for the collection of manganese nodules from the seafloor. However, since the system can be a mobile underwater vehicle itself, the system may be moved to any desired depth and location. Thus, the system can provide electric power at any desired location in the body of water.

The system can store hydrogen gas and oxygen gas for any desired length of time before using the gases to generate electricity. For example, the system can include gas storage tanks such as shown in FIG. 12. This can allow the system to provide electricity generation on demand by using the stored oxygen and hydrogen. In alternative examples, the system can generate the hydrogen and oxygen through the action of the bacterial colonies at the time when electricity is desired, so that the hydrogen and oxygen go directly to the hydrogen fuel cell without being stored.

In further examples, the system for generating electricity in a body of water can be split between two separate unmanned underwater vehicles. A first underwater unmanned vehicle can include the bacterial colonies, reaction chamber, and bubbling chamber for generating the oxygen gas and hydrogen gas. The second underwater unmanned vehicle can include a hydrogen fuel cell generator. In such examples, the second unmanned underwater vehicle can be a vehicle that is powered by a hydrogen fuel cell generator, and which may need to refill a hydrogen tank and an oxygen tank from time to time to continue operating. The first unmanned underwater vehicle can act as refilling station to provide hydrogen gas and oxygen gas. In certain examples, the two vehicles can be dockable such that hydrogen gas and oxygen gas can be transferred from the first vehicle to the second vehicle while the vehicles are docked.

Figure 13:
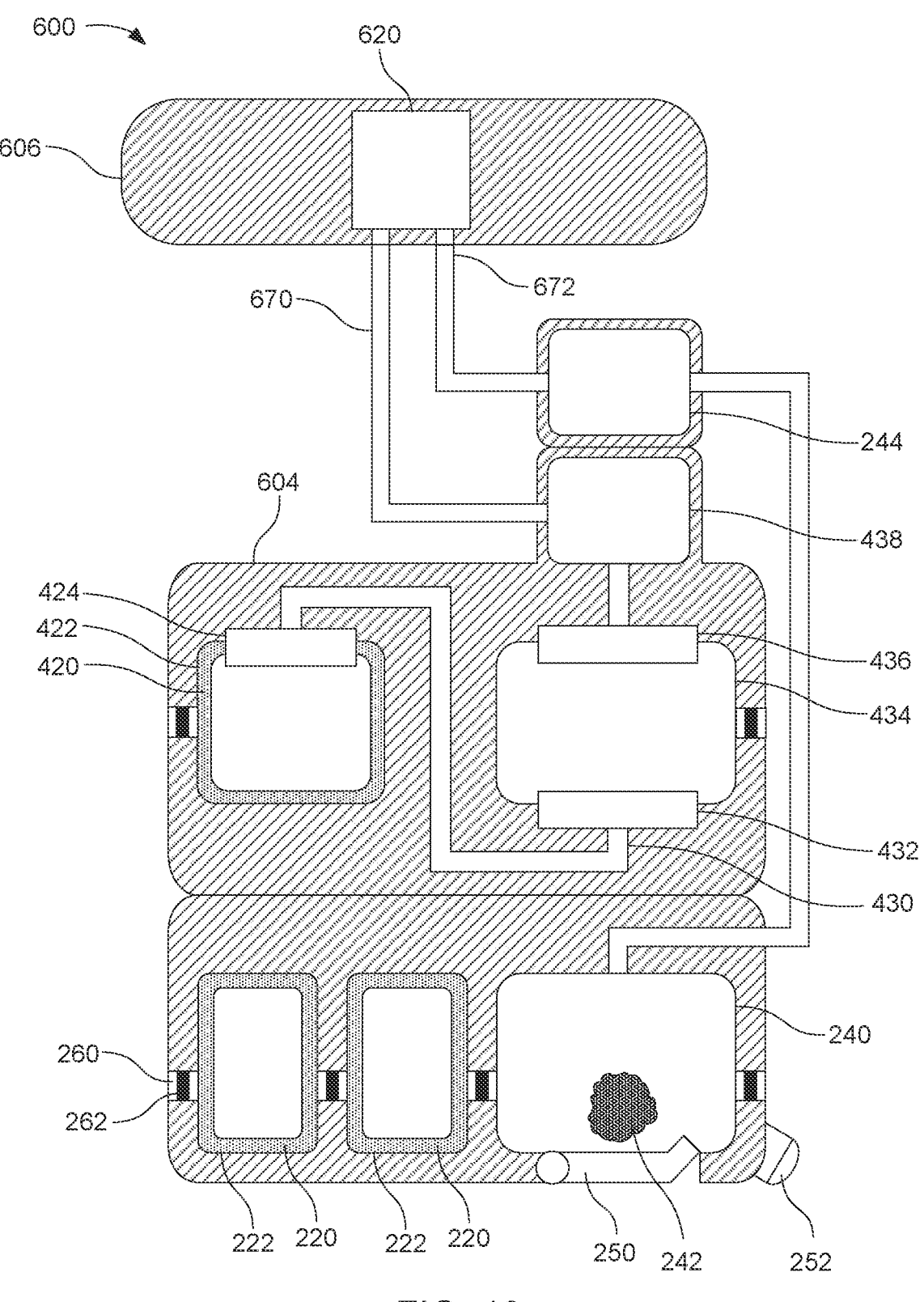
FIG. 13 is a cross-sectional view of another system for generating electricity in a body of water in accordance with still another example of the present invention.

FIG. 13 shows one such example system 600 that includes a first underwater unmanned vehicle 604 and a second underwater unmanned vehicle 606. The first underwater unmanned vehicle includes many of the same components as the system shown in FIG. 12, including bacterial colonies 220, 230, and 420, and the various compartments and chambers shown in FIG. 12. The first underwater unmanned vehicle also includes a hydrogen storage tank 244 and an oxygen/nitrogen gas storage tank 438. These tanks can store the gases until a second unmanned underwater vehicle docks with the first vehicle to refuel. This figure shows the second vehicle docked with the first vehicle, so that hydrogen gas and oxygen gas can flow to the second vehicle through connections 670 and 672. The hydrogen and oxygen can be used by the hydrogen fuel cell generator 620 in the second vehicle to power the second vehicle.

It is to be understood that the examples of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular examples only and is not intended to be limiting.

Reference throughout this specification to "one example" or "an example" means that a particular feature, structure, or characteristic described in connection with the example is included in at least one example of the present invention. Thus, appearances of the phrases "in one example" or "in an example" in various places throughout this specification are not necessarily all referring to the same example.

Although the disclosure may not expressly disclose that some examples or features described herein may be combined or interchanged with other examples or features described herein, this disclosure should be read to describe any such combinations that would be practicable by one of ordinary skill in the art no matter the specific examples that were described. Indeed, unless a certain combination of elements or functions not expressly disclosed would conflict with one another, such that the combination would render the resulting example inoperable or impracticable as would be apparent to those skilled in the art, this disclosure is meant to contemplate that any disclosed element or feature or function in any example described herein can be incorporated into any other example described herein (e.g., the elements or features or functions combined or interchanged with other elements or features or functions across examples) even though such combinations or interchange of elements or features or functions and resulting examples may not have been specifically or expressly disclosed and described. The use of "or" in this disclosure should be understood to mean non-exclusive or, i.e., "and/or," unless otherwise indicated herein.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various examples of the present invention can be referred to herein along with alternatives for the various components thereof. It is understood that such examples and alternatives are not to be construed as de facto equivalents of one another, but are to be considered as separate and autonomous representations of the present invention.

Furthermore, the described features, structures, or characteristics can be combined in any suitable manner in one or more examples. In the description, numerous specific details are provided, such as examples of lengths, widths, shapes, etc., to provide a thorough understanding of examples of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method of generating hydrogen gas, comprising:
providing a colony of sulfur-reducing bacteria and a colony of sulfur-oxidizing bacteria, wherein the colonies are submerged in a body of water;
using the colony of sulfur-reducing bacteria, converting at least a portion of sulfates present in the body of water to hydrogen sulfide;
using the colony of sulfur-oxidizing bacteria, converting the hydrogen sulfide to sulfuric acid; and reacting the sulfuric acid with a manganese nodule originating on a seafloor to produce hydrogen gas and manganese sulfate.

2. The method of claim 1, wherein the colonies are in or on a housing submerged in the body of water.

3. The method of claim 2, wherein the housing comprises a sulfur-reducing compartment and a sulfur-oxidizing compartment, wherein the colony of sulfur-reducing bacteria is in the form of a film on an interior surface of the sulfur-reducing compartment, and wherein the colony of sulfur-oxidizing bacteria is in the form of a film on an interior surface of the sulfur-oxidizing compartment.

4. The method of claim 3, further comprising flowing water from the body of water into the sulfur-reducing compartment and flowing water from the sulfur-reducing compartment into the sulfur-oxidizing compartment.

5. The method of claim 3, wherein the housing further comprises a reaction chamber, wherein the method further comprises flowing water and the sulfuric acid from the sulfur-oxidizing compartment into the reaction chamber, wherein the sulfuric acid is reacted with the manganese in the reaction chamber.

6. The method of claim 5, and wherein the method further comprises collecting the manganese nodule from the seafloor and placing the manganese nodule in the reaction chamber.

7. The method of claim 6, wherein the manganese nodule is collected using a robotic collector.

8. The method of claim 7, wherein the robotic collector comprises an optical sensor to detect the manganese nodule on the seafloor, wherein the method further comprises detecting the manganese nodule based on a characteristic comprising size, shape, orientation, texture, cluster density, or a combination thereof.

9. The method of claim 1, wherein the body of water is an ocean and wherein the colonies are submerged at a depth within about 10 meters of a seafloor of the ocean.

10. The method of claim 1, wherein the sulfur-reducing bacteria convert the sulfates to the hydrogen sulfide through an aerobic sulfate reduction pathway.

11. The method of claim 10, wherein the sulfur-reducing bacteria comprise *Escherichia coli*, *Pseudomonas* spp., *Pseudomonas aeruginosa*, *Vibrio* spp., *Vibrio natriegens*, or a combination thereof.

12. The method of claim 1, wherein the sulfur-oxidizing bacteria comprise neutrophilic sulfur-oxidizing bacteria and acidophilic sulfur-oxidizing bacteria.

13. The method of claim 12, wherein the neutrophilic sulfur-oxidizing bacteria comprise Thiotrix, Thiomonas, Halothiobacillus, or a combination thereof, and wherein the acidophilic sulfur-oxidizing bacteria comprise *Acidothiobacillus thiooxidans*, *Acidothiobacillus ferrooxidans*, or a combination thereof.

14. The method of claim 1, further comprising storing the hydrogen gas or using the hydrogen gas to power a hydrogen fuel cell generator to generate electricity.

* * * * *